US008324261B2

(12) United States Patent
Nakazawa et al.

(10) Patent No.: US 8,324,261 B2
(45) Date of Patent: Dec. 4, 2012

(54) HISTIDINE DERIVATIVES

(75) Inventors: Yoshitaka Nakazawa, Sanda (JP); Kenji Mitsuda, Sanda (JP); Tomohiro Ookubo, Kato (JP); Teppei Seguchi, Kato (JP); Hiroyoshi Nanba, Taka-gun (JP)

(73) Assignee: Nippon Zoki Pharmaceutical Co., Ltd., Osaka (JP)

( * ) Notice: Subject to any disclaimer, the term of this patent is extended or adjusted under 35 U.S.C. 154(b) by 0 days.

(21) Appl. No.: 12/452,533

(22) PCT Filed: Jul. 18, 2008

(86) PCT No.: PCT/JP2008/063046
§ 371 (c)(1),
(2), (4) Date: Feb. 24, 2010

(87) PCT Pub. No.: WO2009/014097
PCT Pub. Date: Jan. 29, 2009

(65) Prior Publication Data
US 2010/0152459 A1    Jun. 17, 2010

(30) Foreign Application Priority Data

Jul. 23, 2007 (JP) ................................ 2007-190928
Dec. 20, 2007 (JP) ................................ 2007-328301

(51) Int. Cl.
*A61K 31/417* (2006.01)
*C07D 233/64* (2006.01)
(52) U.S. Cl. ..................................... 514/400; 548/338.1
(58) Field of Classification Search .................. 514/399, 514/400; 548/338.1
See application file for complete search history.

(56) References Cited

U.S. PATENT DOCUMENTS

2002/0150629 A1    10/2002    Nishimura et al.
2009/0149658 A1 *  6/2009    Nakamura et al. .......... 548/338.1

FOREIGN PATENT DOCUMENTS

| EP | 0 127 076 A2 | 12/1984 |
| JP | A-59-216597 | 12/1984 |
| JP | B2-6-41411 | 6/1994 |
| JP | A-7-97323 | 4/1995 |
| JP | A-9-20660 | 1/1997 |
| JP | A-9-20661 | 1/1997 |
| JP | 10-298197 | * 10/1998 |
| JP | A-10-298197 | 11/1998 |
| JP | B2-2939301 | 6/1999 |
| JP | B2-2939301 | 8/1999 |
| JP | A-2003-267992 | 9/2003 |
| JP | A-2006-232685 | 9/2006 |
| WO | WO 01/91762 A1 | 12/2001 |
| WO | WO 2007/086354 A1 | 8/2007 |
| WO | WO 2007086354 A1 * | 8/2007 |

OTHER PUBLICATIONS

U.S. Appl. No. 2008-87591, commonly assigned to Nippon Zoki Pharmaceutical Company.*
Giron, D. J. Therm. Anal. Cal. 2001, vol. 64, pp. 37-60.*
Giron, D. J. Therm. Anal. Cal. 2002, vol. 68, pp. 335-357.*
B. Rodriquez-Spong et al. Advanced Drug Delivery Reviews, 2004, 56, pp. 241-274.*
Zhao et al., "New agents for cutaneous photoprotection: derivatives of alpha-amino acids, 4-aminobenzoic and 4-methoxycinnamic acids," 1993, pp. 949-954, vol. 28, European Journal of Medicinal Chemistry, France.
Garipcan et al., "A Novel Affinity Support Material for the Separation of Immunoglobulin G from Human Plasma," Macromol. Biosci. 2002, pp. 135-144, vol. 2.
Bentolila et al., "Synthesis and Heparin-like Biological Activity of Amino Acid-based Polymers," 2000, pp. 377-387, vol. 11, Polymers for Advanced Technologies.
Aug. 19, 2008 International Search Report issued in International Application No. PCT/JP2008/063046 (with translation).
Kita et al., Nippon Yakurigaku Zasshi, "Stress state caused by alteration of rhythm in environmental temperature, and the functional disorders in mice and rats," Folia pharmacol.japon, 1975, pp. 195-210, vol. 71 (with Abstract).
Kita et al., Tail Pressure Method, "Analgesic effects of Neurotropin in mice, and comparison between analgesic effects of some drugs in SART-stress mice and normal mice," Nippon Yakurigaku Zasshi, Folia pharmacol.japon, 1976, pp. 573-584, vol. 72 (with Abstract).
Kim et al., "An experimental model for peripheral neuropathy produced by segmental spinal nerve ligation in the rat," Pain, 1992, pp. 355-363, vol. 50.
Lee et al., "Receptor Subtype Mediating the Adrenergic Sensitivity of Pain Behavior and Ectopic Discharges in Neuropathic Lewis Rats," J. Neurophysiol., 1999, pp. 2226-2233, vol. 81.
Chaplan et al., "Quantitative assessment of tactile allodynia in the rat paw," Journal of Neuroscience Methods, 1994, pp. 55-63, vol. 53.
Ohkubo et al.; "Catalytic Activities of Novel L-Histidyl Group-Introduced Polymers Imprinted by a Transition State Analogue in the Hydrolysis of Amino Acid Esters;" Journal of Molecular Catalysis A: Chemical; 1995; pp. L111-L114; vol. 101.
Bentolila et al.; "Poly(N-acryl amino acids): A New Class of Biologically Active Polyanions;" Journal of Medical Chemistry; 2000; pp. 2591-2600; vol. 43.
Cho et al.; "Hydrophobic and Ionic Interactions in the Ester Hydrolysis by Imidazole-Containing Polymers;" Bulletin of Korean Chemical Society; 1982; 34-36; vol. 3, No. 1.
Vippagunta et al., "Crystalline Solids", Advanced Drug Delivery Reviews, 48 (2001), pp. 3-26.
Souillac, et al., Characterization of Delivery Systems, Differential Scanning Calorimetry, pp. 217-218 (in Encyclopedia of Controlled Drug Delivery, 1999, John Wiley & Sons, pp. 212-227).
Jul. 17, 2009 Office Action issued in U.S. Appl. No. 12/087,591.
Nov. 17, 2009 Office Action issued in U.S. Appl. No. 12/087,591.
Giron, D.J., "Applications of Thermal Analysis and Coupled Techniques in Pharmaceutical Industry", Journal of Thermal Analysis and Calorimetry, 2001, vol. 64, pp. 37-60.
Giron, D.J., "Applications of Thermal Analysis and Coupled Techniques in Pharmaceutical Industry", Journal of Thermal Analysis and Calorimetry, 2002, vol. 68, pp. 335-357.
B. Rodriquez-Spong et al., "General Principles of Pharmaceutical Solid Polymorphism: A Supramolecular Perspective", Advanced Drug Delivery Reviews, 2004, 56, pp. 241-274.

* cited by examiner

*Primary Examiner* — Joseph Kosack
*Assistant Examiner* — Matthew Coughlin
(74) *Attorney, Agent, or Firm* — Oliff & Berridge, PLC

(57) ABSTRACT

The present invention is to provide a novel compound which is useful as a pharmaceutical agent such as an analgesic. The present invention is to provide the novel histidine derivative having an excellent analgesic action and the like. The compound of the present invention has a very high intermigration into the blood upon oral administration and is very useful as a pharmaceutical agent, especially an analgesic for the treatment of acute or chronic pain diseases and of neuropathic pain diseases.

19 Claims, 1 Drawing Sheet

[Figures]
[Fig1.]
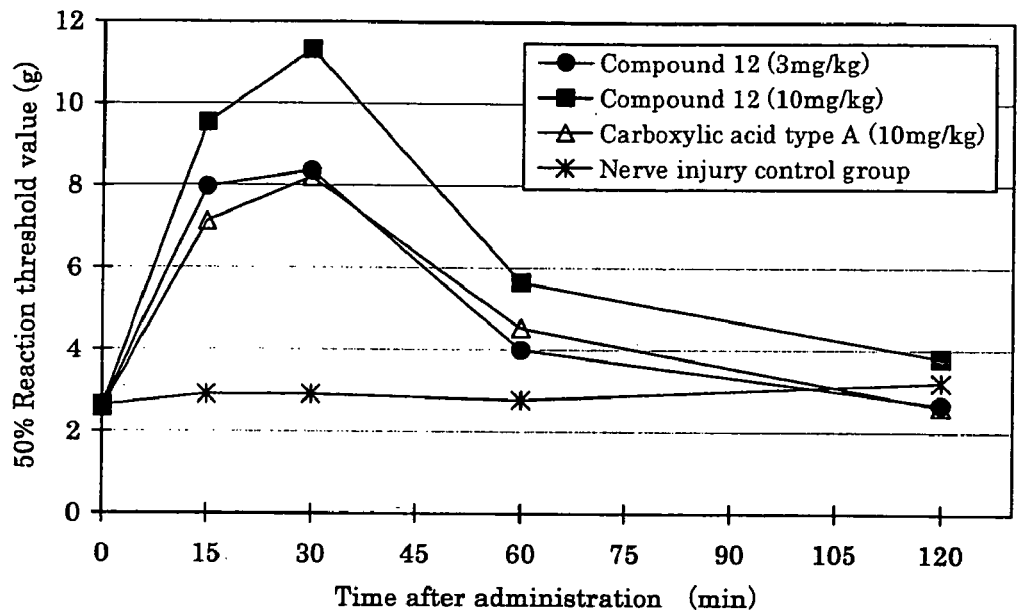
[Fig.2]
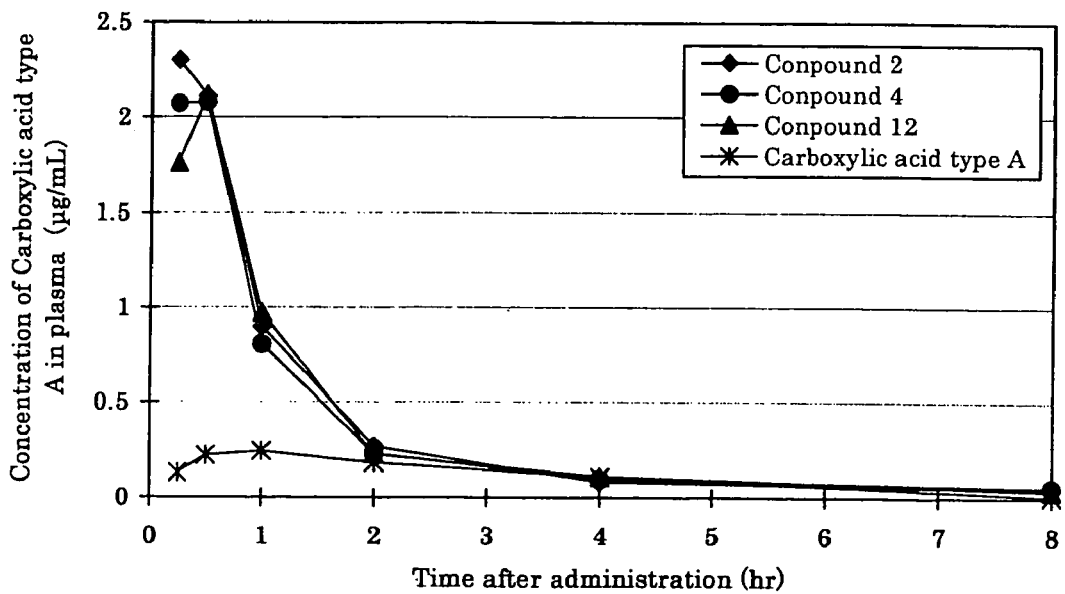

HISTIDINE DERIVATIVES

TECHNICAL FIELD

The present invention relates to a novel histidine derivative and a pharmaceutically acceptable salt and hydrate thereof and also to a pharmaceutical agent containing said compound as an effective ingredient.

BACKGROUND ART

Anserine (N-β-alanyl-1-methyl-L-histidine) or carnosine (β-ananyl-L-histidine) in which β-alanine is bonded to histidine or methylhistidine, respectively is a histidine derivative abundantly available in muscles of mammals, birds, reptiles, amphibian, etc. and has been reported to have various pharmacological actions.

For example, it has been disclosed that anserine has an immunomodulating action (refer to Patent Document 1) and an anti-stress action (refer to Patent Document 2) and that anserine and carnosine have a suppressive action for hypertension (refer to Patent Document 3), a promoting action for iron absorption (refer to Patent Document 4), an enhancing action for learning ability (refer to Patent Document 5), a promoting action for zinc absorption (refer to Patent Document 6) and antioxidant/anti-aging/anti-cancer actions (refer to Patent Document 7). However, there has been no report for their analgesic action.

Patent Document 1: Japanese Examined Patent Publication No. Hei-06/041,411
Patent Document 2: Japanese Patent Laid-Open No. Hei-09/020,660
Patent Document 3: Japanese Patent No. 2,939,301
Patent Document 4: Japanese Patent Laid-Open No. Hei-07/097,323
Patent Document 5: Japanese Patent Laid-Open No. Hei-09/020,661
Patent Document 6: International Publication WO 01/091,762
Patent Document 7: Japanese Patent Laid-Open No. 2003/267,992

DISCLOSURE OF THE INVENTION

Problems that the Invention is to Solve

An object of the present invention is to provide a novel compound which is useful as a pharmaceutical agent, especially an excellent analgesic.

Means for Solving the Problems

The present inventors have carried out intensive studies for the compounds showing an effect to various types of pain. As a result, they have found that a histidine derivative which is a compound where $R_5$ in the following formula (I) is hydrogen (hereinafter, it will be referred to as a "carboxylic acid type") exhibits an excellent analgesic action in pathological animal models suffering from acute or chronic pain or from neuropathic pain. However, since transmigration of such a carboxylic acid type to blood upon its oral administration to the animal is bad, they have carried out further studies. And, they found that the compound of the present invention represented by the following formula (I) has an excellent transmigration to blood upon oral administration as compared with the carboxylic acid type. Incidentally, the compound of the present invention is quickly metabolized to its carboxylic acid type by the action of an esterase in vivo and is detected as a carboxylic acid type in the blood. As such, the novel histidine derivative represented by the following formula (I) exhibits an excellent transmigration to the blood upon oral administration as a prodrug of the carboxylic acid type and, accordingly, it is very useful as a pharmaceutical agent such as an analgesic for the treatment of diseases showing acute or chronic pain or neuropathic pain.

Advantages of the Invention

The histidine derivative of the present invention is a novel compound showing an excellent analgesic action to pathological animal models suffering from acute or chronic pain and neuropathic pain. As compared with the carboxylic acid type thereof, the compound of the present invention has a high transmigration to the blood upon oral administration, and, in the blood, it is present as a carboxylic acid type exhibiting a low toxicity. Accordingly, the compound of the present invention is very useful as a pharmaceutical agent such as an analgesic for the treatment of diseases showing acute or chronic pain or neuropathic pain.

BRIEF DESCRIPTION OF THE DRAWINGS

FIG. 1 is an example of the result where the anti-allodynia action was investigated when Compound 12 of the present invention and Carboxylic acid type A thereof were orally administered to Chung model rats.

FIG. 2 is an example of the result where kinetics in the blood was investigated when the compound of the present invention and a carboxylic acid type thereof were orally administered to rats.

BEST MODE FOR CARRYING OUT THE INVENTION

The present invention relates to a histidine derivative represented by the following formula (I) and a pharmaceutically acceptable salt and hydrate thereof and also to a pharmaceutical agent such as an analgesic containing said compound as an effective ingredient.

[chem. 1]

(I)

[In the formula, $R_1$ is hydrogen, alkyl having 1 to 6 carbon(s) or benzyl which may be substituted with alkyl having 1 to 4 carbon(s) or halogen; $R_2$ is hydrogen or alkyl having 1 to 4 carbon(s); $R_3$ and $R_4$ are same or different and each is hydrogen, alkyl having 1 to 4 carbon(s) or phenyl which may be substituted with any one or two of alkyl having 1 to 6 carbon(s), alkoxy having 1 to 6 carbon(s), hydroxy, halogen, trifluoromethyl, nitro and cyano; and $R_5$ is alkyl having 1 to 8 carbon(s), carboxyl-alkyl having 1 to 4 carbon(s), alkoxy having 1 to 4 carbon(s)-carbonyl-alkyl having 1 to 4 carbon(s), 1-(cyclohexyloxycarbonyloxy)ethyl or one or two phenyl(s)-alkyl having 1 to 4 carbon(s) which may be substituted with alkyl having 1 to 6 carbon(s), alkoxy having 1 to 4 carbon(s) or halogen.]

In the substituent for the above formula (I), alkyl having 1 to 6 carbon(s) is preferably a linear or branched alkyl group such as methyl, ethyl, propyl, isopropyl, butyl, isobutyl, sec-butyl, tert-butyl, pentyl, isopentyl, neopentyl, tert-pentyl, hexyl and isohexyl, and alkyl having 1 to 4 carbon(s) is preferably a linear or branched alkyl group such as methyl, ethyl, propyl, isopropyl, butyl, isobutyl, sec-butyl and tert-butyl.

Alkoxy having 1 to 6 carbon(s) is preferably a linear or branched alkoxy group such as methoxy, ethoxy, propyloxy, isopropyloxy, butyloxy, pentyloxy and hexyloxy, and alkoxy having 1 to 4 carbon(s) is preferably a linear or branched alkoxy group such as methoxy, ethoxy, propyloxy, isopropyloxy and butyloxy.

Halogen is fluoro, chloro, bromo, iodo, etc.

The phenylalkyl of $R_5$ is may be substituted with alkyl, alkoxy or halogen, and each substituent is substituted at a phenyl group moiety of the phenylalkyl.

Preferred compounds of the present invention are indicated as follows.

$N^\alpha$-acryloyl-$N^\pi$-methyl-L-histidine methyl ester [Compound 1]

$N^\alpha$-acryloyl-$N^\pi$-methyl-L-histidine ethyl ester [Compound 2]

$N^\alpha$-acryloyl-$N^\pi$-methyl-L-histidine neopentyl ester [Compound 3]

$N^\alpha$-acryloyl-$N^\pi$-methyl-L-histidine isopentyl ester [Compound 4]

$N^\alpha$-acryloyl-$N^\pi$-methyl-L-histidine 3,3-dimethylbutyl ester [Compound 5]

$N^\alpha$-acryloyl-$N^\pi$-methyl-L-histidine butyl ester [Compound 6]

$N^\alpha$-acryloyl-$N^\pi$-methyl-L-histidine octyl ester [Compound 7]

$N^\alpha$-acryloyl-$N^\pi$-methyl-L-histidine benzyl ester [Compound 8]

$N^\alpha$-acryloyl-$N^\pi$-methyl-L-histidine 4-methylbenzyl ester [Compound 9]

$N^\alpha$-acryloyl-$N^\pi$-methyl-L-histidine 4-chlorobenzyl ester [Compound 10]

$N^\alpha$-acryloyl-$N^\pi$-methyl-L-histidine 4-tert-butylbenzyl ester [Compound 11]

$N^\alpha$-acryloyl-$N^\pi$-methyl-L-histidine phenethyl ester [Compound 12]

$N^\alpha$-acryloyl-$N^\pi$-methyl-L-histidine 4-methoxyphenethyl ester [Compound 13]

$N^\alpha$-acryloyl-$N^\pi$-methyl-L-histidine 4-methylphenethyl ester [Compound 14]

$N^\alpha$-acryloyl-$N^\pi$-methyl-L-histidine 4-chlorophenethyl ester [Compound 15]

$N^\alpha$-acryloyl-$N^\pi$-methyl-L-histidine 4-tert-butylphenethyl ester [Compound 16]

$N^\alpha$-acryloyl-$N^\pi$-methyl-L-histidine 1-(cyclohexyloxycarbonyloxy)ethyl ester [Compound 17]

$N^\alpha$-acryloyl-$N^\pi$-methyl-L-histidine ethoxycarbonylmethyl ester [Compound 18]

$N^\alpha$-acryloyl-$N^\pi$-methyl-L-histidine carboxylmethyl ester [Compound 19]

$N^\alpha$-3-phenylacryloyl-$N^\pi$-ethyl-L-histidine phenethyl ester [Compound 20]

$N^\alpha$-acryloyl-$N^\pi$-benzyl-L-histidine phenethyl ester [Compound 21]

$N^\alpha$-tigloyl-$N^\pi$-methyl-L-histidine phenethyl ester [Compound 22]

$N^\alpha$-crotonoyl-$N^\pi$-methyl-L-histidine phenethyl ester [Compound 23]

$N^\alpha$-acryloyl-$N^\pi$-methyl-L-histidine diphenylmethyl ester [Compound 24]

$N^\alpha$-acryloyl-$N^\pi$-methyl-L-histidine 1,1-dimethyl-2-phenethyl ester [Compound 25]

$N^\alpha$-[3-(2-hydroxyphenyl)acryloyl]-$N^\pi$-methyl-L-histidine phenethyl ester hydrochloride [Compound 26]

As hereunder, a general process for producing the compound of the present invention will be shown. The compound of the present invention, represented by the above formula (I) is a histidine derivative in which an alkyl group or hydrogen is on a π-nitrogen atom of an imidazole ring and is able to be produced by the process mentioned below. Some compounds, which are produced by other than the process mentioned below, are able to be produced pursuant to Examples described below. As hereunder, examples of a process for producing an L-substance of the histidine derivative which is the compound of the present invention will be shown and a D-substance which is a stereoisomer thereof is also able to be synthesized by the same route.

<Production Process 1>

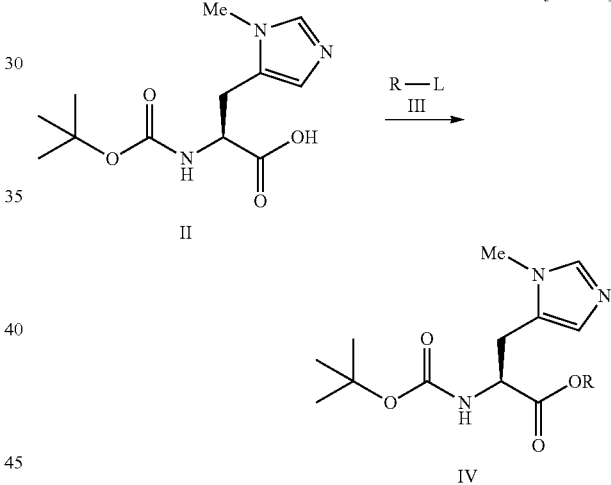

[Scheme 1]

[chem. 2]

L in the scheme 1 is a hydroxyl group or halogen and, with regard to the halogen, preferably used ones thereof include bromine, chlorine and iodine.

When L is a hydroxyl group, equivalent to excessive amounts of $N^\alpha$-tert-butoxycarbonyl-$N^\pi$-methyl-L-histidine (II) and an alcohol (III) were used and made to react at room temperature usually for 1 hour to 3 days together with a condensing agent such as a water-soluble carbodiimide hydrochloride (WSC.HCl) in the presence of a catalytic amount of N,N-dimethyl-4-aminopyridine (DMAP) in an inert solvent. Examples of the solvent include a halogenated hydrocarbon solvent (such as methylene chloride), an ether solvent (such as tetrahydrofuran (THF)), dimethylformamide (DMF) and dimethyl sulfoxide (DMSO).

When L is halogen, equivalent to excessive amounts of the compound (II) and the alkylating agent (III) were used and made to react at room temperature usually for 1 hour to 24 days in the presence of a base in an inert solvent. Examples of the solvent include a halogenated hydrocarbon solvent (such as methylene chloride), an ether solvent (such as THF), DMF and DMSO. Examples of the base include an inorganic base such as potassium carbonate, sodium carbonate, potassium hydrogen carbonate or sodium hydrogen carbonate.

<Production Process 2>

[Scheme 2]

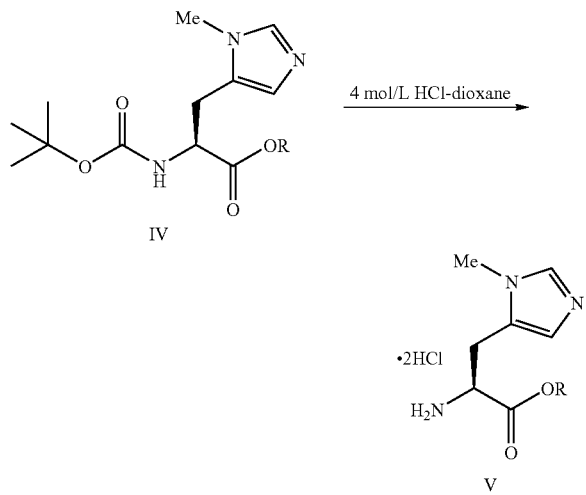

The compound (IV) and a 4 mol/L hydrogen chloride-dioxane solution were used excessively and made to react at room temperature usually for 1 hour to 4 hours in an inert solvent. Examples of the solvent include a halogenated hydrocarbon solvent such as methylene chloride.

<Production Process 3>

[Scheme 3]

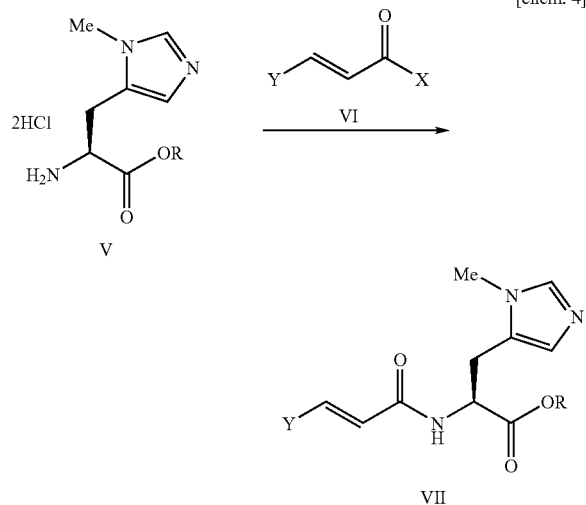

Equivalent to excessive amounts of the compound (V) and the compound (VI) were used and, when X is Cl, they were made to react at from 0° C. to room temperature in the presence of an excessive amount of a base in water or in methylene chloride whereupon the compound (WI) is able to be produced. When X is OH, they were made to react at room temperature using an equivalent to excessive amount of WSC.HCl or DCC in the presence of an excessive amount of a base in methylene chloride whereupon the compound (VII) is able to be produced. Examples of the base include an inorganic base such as potassium hydrogen carbonate or sodium hydrogen carbonate and an organic base such as triethylamine or morpholine. When a protective group is bonded to Y, it is appropriately removed therefrom whereupon the compound (VII) is able to be produced.

The compounds represented by the above-given formula (I) include the pharmaceutically acceptable salts of thereof such as acid addition salts with hydrochloric acid, sulfuric acid, nitric acid, hydrobromic acid, phosphoric acid, perchloric acid, thiocyanic acid, boric acid, formic acid, acetic acid, haloacetic acid, propionic acid, glycolic acid, citric acid, tartaric acid, succinic acid, gluconic acid, lactic acid, malonic acid, fumaric acid, anthranilic acid, benzoic acid, cinnamic acid, p-toluenesulfonic acid, naphthalenesulfonic acid or sulfanilic acid; salts with alkali metal such as sodium or potassium, salts with alkaline-earth metal such as calcium or magnesium, or salts with other metals such as aluminum; or salts with bases such as ammonia or organic amines. Those salts may be manufactured by known methods from the compounds of the present invention in a free state or may be mutually converted among the salts. When the compounds are present in the state of a steric isomer such as cis-trans isomer, optical isomer and conformational isomer, or a solvate such as a hydrate or a metal complex compound, the present invention includes any and all of them.

The compound of the present invention can be made into pharmaceutical preparations by a combination with a suitable pharmaceutical carriers or diluents according to any conventional methods, for example, an oral preparation (e.g. tablets, capsules, powders, liquids, etc.) and a parenteral preparation (e.g. for subcutaneous, intravenous, intramuscular, intrarectal and intranasal administrations). In the prescription, the compound of the present invention may also be used in the form of the pharmaceutically acceptable salt thereof wherein it is able to be used either solely or jointly by an appropriate combination. It may be made into a compounded agent with other pharmaceutically effective ingredients.

The preferred dose of the compound of the present invention may vary depending upon the subject to be administered, dosage form, the administration method, the period for administration, etc. and, in order to achieve a desired effect, 0.5-1000 mg per day may be usually given to common adults by oral route either once daily or several times a day. In the case of a parenteral administration such as by injection, the daily dose is preferably from ⅓ to ¹/₁₀ the dose level for each of the doses mentioned above.

EXAMPLES

Melting point was measured by a melting point measuring device of Yamato MP-21 type and was not corrected. Nuclear magnetic resonance spectrum ($^1$H-NMR) was measured by a nuclear magnetic resonance device of Bruker ARX-500 type and TMS ($\delta=0$) was used as an internal standard. Optical rotation was measured by a polarimeter of JASCO DP-140 type. A silica gel column chromatography was carried out using silica gel DM 1020 for chromatography of an aminopropyl group bonding type and silica gel BW-127ZH for common normal phase chromatography (both manufactured by Fuji Silicia K. K.). In a thin layer chromatography, Silica gel F254 (Merck, No. 5715) was used and detection was conducted using a LTV lamp and a 5% phosphomolybdic acid-ethanol color reagent. With regard to the reagents and the solvents, commercially available ones were used just as they were.

Example 1

Production of $N^\pi$-methyl-L-histidine methyl ester dihydrochloride

Into a solution of $N^\alpha$-tert-butoxycarbonyl-$N^\pi$-methyl-L-histidine methyl ester (17.2 g, 61.0 mmol) in methylene chloride (350 mL) was dropped a 4 mol/L hydrogen chloride-dioxane solution (152 mL, 610 mmol HCl) at room temperature. After stirring the mixture for 4 hours, the solvent was evaporated therefrom in vacuo and diethyl ether was added to the resulting oily residue to give the title compound (15.5 g, 99%) as crystals.

$^1$H-NMR (DMSO-$d_6$) δ: 3.36-3.38 (m, 2H), 3.77 (s, 3H), 3.85 (s, 3H), 4.41-4.43 (m, 1H), 7.59 (s, 1H), 9.04 (s, 2H), 9.14 (s, 1H).

Example 2

Production of $N^\alpha$-acryloyl-$N^\pi$-methyl-L-histidine methyl ester [Compound 1]

To a solution of $N^\pi$-methyl-L-histidine methyl ester dihydrochloride (2.0 g, 7.8 mmol) in water (25 mL) was added potassium hydrogen carbonate (3.1 g, 31.2 mmol) at 0° C. and the mixture was stirred for 15 minutes as it was. After that, acryloyl chloride (1.1 mL, 13.7 mmol) was added thereto at 0° C. and the mixture was stirred for 1 hour as it was. Methylene chloride was added to the residue prepared by evaporation of the solvent in vacuo and the insoluble matter was removed therefrom. The filtrate was dried over anhydrous sodium sulfate in the presence of a small amount of silica gel and the solvent was evaporated therefrom in vacuo to give the title compound (1.2 g, 66%) as an oily substance.

$^1$H-NMR (DMSO-$d_6$) δ: 2.96 (dd, J=8.8, 15.5 Hz, 1H), 3.05 (dd, J=5.4, 15.5 Hz, 1H), 3.53 (s, 3H), 3.63 (s, 3H), 4.58-4.63 (m, 1H), 5.63 (dd, J=2.0, 10.2 Hz, 1H), 6.10 (dd, J=2.0, 17.1 Hz, 1H), 6.28 (dd, J=10.2, 17.1 Hz, 1H), 6.63 (s, 1H), 7.49 (s, 1H), 8.60 (d, J=7.8 Hz, 1H).

Example 3

Production of $N^\pi$-methyl-L-histidine ethyl ester dihydrochloride

The title compound (3.6 g, 99%) was produced as crystals starting from $N^\alpha$-tert-butoxycarbonyl-$N^\pi$-methyl-L-histidine ethyl ester (4.0 g, 13.5 mmol), a 4 mol/L hydrogen chloride-dioxane solution (33.6 mL, 135 mmol HCl) and methylene chloride (80 mL) in the same manner as in the case of $N^\pi$-methyl-L-histidine methyl ester dihydrochloride.

$^1$H-NMR (DMSO-$d_6$) δ: 1.21 (t, J=7.2 Hz, 3H), 3.34-3.36 (m, 2H), 3.85 (s, 3H), 4.21 (q, J=7.2 Hz, 2H), 3.39-4.41 (m, 1H), 7.59 (s, 1H), 8.96 (s, 2H), 9.13 (s, 1H).

Example 4

Production of $N^\alpha$-acryloyl-$N^\pi$-methyl-L-histidine ethyl ester [Compound 2]

The title compound (2.2 g, 67%) was produced as an oily substance starting from $N^\pi$-methyl-L-histidine ethyl ester dihydrochloride (3.6 g, 13.3 mmol), potassium hydrogen carbonate (5.3 g, 53.2 mmol), acryloyl chloride (1.9 mL, 23.3 mmol) and water (60 mL) in the same manner as in the case of $N^\alpha$-acryloyl-$N^\pi$-methyl-L-histidine methyl ester.

$^1$H-NMR (DMSO-$d_6$) δ: 1.14 (t, J=7.0 Hz, 3H), 2.96 (dd, J=8.5, 15.4 Hz, 1H), 3.03 (dd, J=5.9, 15.4 Hz, 1H), 3.54 (s, 3H), 4.08 (q, J=7.0 Hz, 2H), 4.57-4.60 (m, 1H), 5.63 (dd, J=1.9, 10.2 Hz, 1H), 6.10 (dd, J=1.9, 17.1 Hz, 1H), 6.29 (dd, J=10.2, 17.1 Hz, 1H), 6.64 (s, 1H), 7.49 (s, 1H), 8.60 (d, J=7.7 Hz, 1H).

Example 5

Production of $N^\alpha$-tert-butoxycarbonyl-$N^\pi$-methyl-L-histidine neopentyl ester To a suspension of $N^\alpha$-tert-butoxycarbonyl-$N^\pi$-methyl-L-histidine (3.0 g, 11.1 mmol) and neopentyl alcohol (1.1 g, 12.3 mmol) in methylene chloride (70 mL) were added WSC.HCl (2.3 g, 12.3 mmol) and DMAP (0.12 g, 1.0 mmol) at 0° C. After the mixture was stirred at room temperature for 20 hours, the reaction mixture was washed with water and dried over anhydrous sodium sulfate. The residue prepared by evaporation of the solvent therefrom in vacuo was purified by silica gel column chromatography (chloroform:methanol=50:1) to give the title compound (3.1 g, 83%) as an oily substance.

$^1$H-NMR (DMSO-$d_6$) δ: 0.89 (s, 9H), 1.36 (s, 9H), 2.89-2.92 (m, 1H), 2.95-2.98 (m, 1H), 3.54 (s, 3H), 3.74 (s, 2H), 4.20-4.21 (m, 1H), 6.65 (s, 1H), 7.35 (d, J=7.9 Hz, 1H), 7.48 (s, 1H).

Example 6

Production of $N^\pi$-methyl-L-histidine neopentyl ester dihydrochloride

The title compound (2.5 g, 87%) was produced as an amorphous solid starting from $N^\alpha$-tert-butoxycarbonyl-$N^\pi$-methyl-L-histidine neopentyl ester (3.1 g, 9.2 mmol), a 4 mol/L hydrogen chloride-dioxane solution (23 mL, 91.9 mmol HCl) and methylene chloride (70 mL) in the same manner as in the case of $N^\pi$-methyl-L-histidine methyl ester dihydrochloride.

$^1$H-NMR (DMSO-$d_6$) δ: 0.90 (s, 9H), 3.37 (dd, J=6.8, 15.8 Hz, 1H), 3.39 (dd, J=7.4, 15.8 Hz, 1H), 3.57 (s, 3H), 3.83-3.89 (m, 2H), 4.47-4.49 (m, 1H), 7.62 (s, 1H), 9.08 (s, 2H), 9.18 (s, 1H).

Example 7

Production of $N^\alpha$-acryloyl-$N^\pi$-methyl-L-histidine neopentyl ester [Compound 3]

The title compound (1.1 g, 45%) was produced as an oily substance starting from $N^\pi$-methyl-L-histidine neopentyl ester dihydrochloride (2.5 g, 8.0 mmol), potassium hydrogen carbonate (3.2 g, 32.2 mmol), acryloyl chloride (1.2 mL, 14.1 mmol) and water (30 mL) in the same manner as in the case of $N^\alpha$-acryloyl-$N^\pi$-methyl-L-histidine methyl ester.

$^1$H-NMR (DMSO-$d_6$) δ: 0.86 (s, 9H), 2.98 (dd, J=8.9, 15.5 Hz, 1H), 3.06 (dd, J=5.6, 15.5 Hz, 1H), 3.54 (s, 3H), 3.70-3.77 (m, 2H), 4.59-4.63 (m, 1H), 5.62 (dd, J=1.4, 10.2 Hz, 1H), 6.10 (dd, J=1.4, 17.0 Hz, 1H), 6.28 (dd, J=10.2, 17.0 Hz, 1H), 6.64 (s, 1H), 7.49 (s, 1H), 8.59 (d, J=7.8 Hz, 1H).

Example 8

Production of N$^\alpha$-tert-butoxycarbonyl-N$^\pi$-methyl-L-histidine isopentyl ester The title compound (3.0 g, 80%) was produced as an oily substance starting from N$^\alpha$-tert-butoxycarbonyl-N$^\pi$-methyl-L-histidine (3.0 g, 11.1 mmol), isopentyl alcohol (1.1 g, 12.0 mmol), WSC.HCl (2.3 g, 12.3 mmol), DMAP (0.12 g, 1.0 mmol) and methylene chloride (42 mL) in the same manner as in the case of N$^\alpha$-tert-butoxycarbonyl-N$^\pi$-methyl-L-histidine neopentyl ester.
$^1$H-NMR (DMSO-d$_6$) δ: 0.87 (d, J=5.7 Hz, 6H), 1.36 (s, 9H), 1.41-1.45 (m, 2H), 1.60-1.65 (m, 1H), 2.86-2.89 (m, 1H), 2.94-2.98 (m, 1H), 3.53 (s, 3H), 4.06 (t, J=6.6 Hz, 2H), 4.15-4.19 (m, 1H), 6.64 (s, 1H), 7.33 (d, J=7.9 Hz, 1H), 7.48 (s, 1H).

Example 9

Production of N$^\pi$-methyl-L-histidine isopentyl ester dihydrochloride

The title compound (2.2 g, 83%) was produced as crystals starting from N$^\alpha$-tert-butoxycarbonyl-N$^\pi$-methyl-L-histidine isopentyl ester (2.8 g, 8.2 mmol), a 4 mol/L hydrogen chloride-dioxane solution (21 mL, 82.0 mmol HCl) and methylene chloride (50 mL) in the same manner as in the case of N$^\pi$-methyl-L-histidine methyl ester dihydrochloride.
$^1$H-NMR (DMSO-d$_6$) δ: 0.87 (d, J=5.7 Hz, 6H), 1.46-1.50 (m, 2H), 1.58-1.64 (m, 1H), 3.31-3.37 (m, 2H), 3.71 (s, 3H), 4.19 (t, J=6.7 Hz, 21), 4.39-4.42 (m, 1H), 7.59 (s, 1H), 9.14 (s, 1H).

Example 10

Production of N$^\alpha$-acryloyl-N$^\pi$-methyl-L-histidine isopentyl ester [Compound 4]

The title compound (0.23 g, 12%) was produced as an oily substance starting from N$^\pi$-methyl-L-histidine isopentyl ester dihydrochloride (2.8 g, 8.2 mmol), potassium hydrogen carbonate (2.6 g, 25.6 mmol), acryloyl chloride (0.9 mL, 11.2 mmol) and water (30 mL) in the same manner as in the case of N$^\alpha$-acryloyl-N$^\pi$-methyl-L-histidine methyl ester.
$^1$H-NMR (DMSO-d$_6$) δ: 0.84-0.86 (m, 6H), 1.40-1.44 (m, 2H), 1.56-1.62 (m, 1H), 2.96 (dd, J=8.6, 15.4 Hz, 1H), 3.03 (dd, J=5.9, 15.4 Hz, 1H), 3.53 (s, 3H), 4.05-4.08 (m, 2H), 4.54-4.59 (m, 1H), 5.63 (dd, J=2.0, 10.2 Hz, 1H), 6.09 (dd, J=2.0, 17.1 Hz, 1H), 6.28 (dd, J=10.2, 17.1 Hz, 1H), 6.63 (s, 1H), 7.49 (s, 1H), 8.59 (d, J=7.7 Hz, 1H).

Example 11

Production of N$^\alpha$-tert-butoxycarbonyl-N$^\pi$-methyl-L-histidine 3,3-dimethylbutyl ester The title compound (2.0 g, 50%) was produced as crystals starting from N$^\alpha$-tert-butoxycarbonyl-N$^\pi$-methyl-L-histidine (3.0 g, 11.1 mmol), 3,3-dimethylbutyl alcohol (1.3 g, 12.3 mmol), WSC.HCl (2.3 g, 12.3 mmol), DMAP (0.12 g, 1.0 mmol) and methylene chloride (70 mL) in the same manner as in the case of N$^\alpha$-tert-butoxycarbonyl-N$^\pi$-methyl-L-histidine neopentyl ester.
$^1$H-NMR (DMSO-d$_6$) δ: 0.90 (s, 9H), 1.35 (s, 9H), 1.46 (t, J=7.2 Hz, 2H), 2.87 (dd, J=8.6, 15.2 Hz, 1H), 2.96 (dd, J=5.5, 15.2 Hz, 1H), 3.53 (s, 3H), 4.07 (t, J=7.2 Hz, 2H), 4.14-4.18 (m, 1H), 6.64 (s, 1H), 7.31 (d, J=7.9 Hz, 1H), 7.48 (s, 1H).

Example 12

Production of N$^\pi$-methyl-L-histidine 3,3-dimethylbutyl ester dihydrochloride The title compound (1.8 g, 95%) was produced as an amorphous solid starting from N$^\alpha$-tert-butoxycarbonyl-N$^\pi$-methyl-L-histidine 3,3-dimethylbutyl ester (2.0 g, 5.7 mmol), a 4 mol/L hydrogen chloride-dioxane solution (14 mL, 56.6 mmol HCl) and methylene chloride (40 mL) in the same manner as in the case of N$^\pi$-methyl-L-histidine methyl ester dihydrochloride.
$^1$H-NMR (DMSO-d$_6$) δ: 0.91 (s, 9H), 1.51 (t, J=6.8 Hz, 2H), 3.34-3.37 (m, 2H), 3.85 (s, 3H), 4.20 (t, J=6.8 Hz, 2H), 4.37-4.79 (m, 1H), 7.60 (s, 1H), 9.00 (s, 2H), 9.15 (s, 1H).

Example 13

Production of N$^\alpha$-acryloyl-N$^\pi$-methyl-L-histidine 3,3-dimethylbutyl ester [Compound 5]

The title compound (1.0 g, 61%) was produced as an oily substance starting from N$^\pi$-methyl-L-histidine 3,3-dimethylbutyl ester dihydrochloride (1.8 g, 5.4 mmol), potassium hydrogen carbonate (2.2 g, 21.4 mmol), acryloyl chloride (0.8 mL, 9.4 mmol) and water (20 mL) in the same manner as in the case of N$^\alpha$-acryloyl-N$^\pi$-methyl-L-histidine methyl ester.
$^1$H-NMR (DMSO-d$_6$) δ: 0.89 (s, 9H), 1.46 (t, J=7.3 Hz, 2H), 2.95 (dd, J=8.8, 15.4 Hz, 1H), 3.03 (dd, J=5.8, 15.4 Hz, 1H), 3.53 (s, 3H), 4.07-4.10 (m, 2H), 4.55-4.58 (m, 1H), 5.62 (dd, J=1.9, 10.2 Hz, 1H), 6.09 (dd, J=1.9, 17.1 Hz, 1H), 6.27 (dd, J=10.2, 17.1 Hz, 1H), 6.33 (s, 1H), 7.49 (s, 1H), 8.58 (d, J=7.8 Hz, 1H).

Example 14

Production of N$^\alpha$-tert-butoxycarbonyl-N$^\pi$-methyl-L-histidine butyl ester The title compound (2.3 g, 89%) was produced as an oily substance starting from N$^\alpha$-tert-butoxycarbonyl-N$^\pi$-methyl-L-histidine (2.0 g, 7.4 mmol), n-butyl alcohol (0.8 g, 8.8 mmol), WSC.HCl (1.6 g, 8.8 mmol), DMAP (0.08 g, 0.72 mmol) and methylene chloride (28 mL) in the same manner as in the case of N$^\alpha$-tert-butoxycarbonyl-N$^\pi$-methyl-L-histidine neopentyl ester.
$^1$H-NMR (DMSO-d$_6$) δ: 0.87 (t, J=7.3 Hz, 3H), 1.28-1.34 (m, 2H), 1.36 (s, 9H), 1.48-1.53 (m, 2H), 2.88 (dd, J=9.5, 15.4 Hz, 1H), 2.96 (dd, J=5.5, 15.4 Hz, 1H), 3.53 (s, 3H), 4.03 (t, J=6.4 Hz, 2H), 4.16-4.18 (m, 1H), 6.64 (s, 1H), 7.32 (d, J=8.0 Hz, 1H), 7.48 (s, 1H).

Example 15

Production of N$^\pi$-methyl-L-histidine butyl ester dihydrochloride

The title compound (1.1 g, 60%) was produced as an amorphous solid starting from N$^\alpha$-tert-butoxycarbonyl-N$^\pi$-methyl-L-histidine butyl ester (2.0 g, 6.1 mmol), a 4 mol/L hydrogen chloride-dioxane solution (15 mL, 60.5 mmol HCl) and methylene chloride (30 mL) in the same manner as in the case of N$^\pi$-methyl-L-histidine methyl ester dihydrochloride.

¹H-NMR (DMSO-d₆) δ: 0.89 (t, J=7.4 Hz, 3H), 1.29-1.33 (m, 2H), 1.54-1.59 (m, 2H), 3.34-3.36 (m, 2H), 3.85 (s, 3H), 3.97 (s, 2H), 4.17 (t, J=6.5 Hz, 2H), 4.41-4.43 (m, 1H), 7.59 (s, 1H), 8.96 (s, 2H), 9.13 (s, 1H).

Example 16

Production of N$^\alpha$-acryloyl-N$^\pi$-methyl-L-histidine butyl ester [Compound 6]

The title compound (0.63 g, 62%) was produced as an oily substance starting from N$^\pi$-methyl-L-histidine butyl ester dihydrochloride (1.1 g, 3.6 mmol), potassium hydrogen carbonate (1.4 g, 14.5 mmol), acryloyl chloride (0.5 mL, 6.3 mmol) and water (20 mL) in the same manner as in the case of N$^\alpha$-acryloyl-N$^\pi$-methyl-L-histidine methyl ester.

¹H-NMR (DMSO-d₆) δ: 0.86 (t, J=7.4 Hz, 3H), 1.26-1.30 (m, 2H), 1.52-1.49 (m, 2H), 2.97 (dd, J=8.5, 15.4 Hz, 1H), 3.02 (dd, J=5.9, 15.4 Hz, 1H), 3.53 (s, 3H), 4.02-4.05 (m, 2H), 4.56-4.58 (m, 1H), 5.63 (dd, J=2.0, 10.2 Hz, 1H), 6.10 (dd, J=2.0, 17.1 Hz, 1H), 6.28 (dd, J=10.2, 17.1 Hz, 1H), 6.63 (s, 1H), 7.49 (s, 1H), 8.59 (d, J=8.0 Hz, 1H).

Example 17

Production of N$^\alpha$-tert-butoxycarbonyl-N$^\pi$-methyl-L-histidine octyl ester The title compound (3.3 g, 77%) was produced as an oily substance starting from N$^\alpha$-tert-butoxycarbonyl-N$^\pi$-methyl-L-histidine (3.0 g, 11.1 mmol), n-octyl alcohol (1.9 g, 12.3 mmol), WSC.HCl (2.3 g, 12.3 mmol), DMAP (0.12 g, 1.0 mmol) and methylene chloride (70 mL) in the same manner as in the case of N$^\alpha$-tert-butoxycarbonyl-N$^\pi$-methyl-L-histidine neopentyl ester.

¹H-NMR (DMSO-d₆) δ: 0.86 (t, J=6.6 Hz, 3H), 1.25-1.31 (m, 10H), 1.36 (s, 9H), 1.50-1.51 (m, 2H), 2.88 (dd, J=9.6, 15.4 Hz, 1H), 2.96 (dd, J=5.3, 15.4 Hz, 1H), 3.53 (s, 3H), 4.01 (t, J=6.5 Hz, 2H), 4.14-4.19 (m, 1H), 6.64 (s, 1H), 7.33 (d, J=7.9 Hz, 1H), 7.48 (s, 1H).

Example 18

Production of N$^\pi$-methyl-L-histidine octyl ester dihydrochloride

The title compound (2.7 g, 89%) was produced as crystals starting from N$^\alpha$-tert-butoxycarbonyl-N$^\pi$-methyl-L-histidine octyl ester (3.3 g, 8.5 mmol), a 4 mol/L hydrogen chloride-dioxane solution (21 mL, 85.4 mmol HCl) and methylene chloride (60 mL) in the same manner as in the case of N$^\pi$-methyl-L-histidine methyl ester dihydrochloride.

¹H-NMR (DMSO-d₆) δ: 0.85-0.86 (m, 3H), 1.24-1.26 (m, 10H), 1.56-1.57 (m, 2H), 3.34-3.37 (m, 2H), 3.85 (s, 3H), 4.14-4.17 (m, 2H), 4.40-4.42 (m, 1H), 7.59 (s, 1H), 9.00 (s, 2H), 9.15 (s, 1H).

Example 19

Production of N$^\alpha$-acryloyl-N$^\pi$-methyl-L-histidine octyl ester [Compound 7]

The title compound (0.4 g, 16%) was produced as an oily substance starting from N$^\pi$-methyl-L-histidine octyl ester dihydrochloride (2.6 g, 7.3 mmol), potassium hydrogen carbonate (2.9 g, 29.4 mmol), acryloyl chloride (1.0 mL, 12.8 mmol) and water (30 mL) in the same manner as in the case of N$^\alpha$-acryloyl-N$^\pi$-methyl-L-histidine methyl ester.

¹H-NMR (DMSO-d₆) δ: 0.80 (t, J=6.5 Hz, 3H), 1.20-1.22 (m, 10H), 1.50-1.52 (m, 2H), 2.98 (dd, J=8.7, 15.5 Hz, 1H), 3.10 (dd, J=5.8, 15.5 Hz, 1H), 3.56 (s, 3H), 4.03 (t, J=6.5 Hz, 2H), 4.64-4.67 (m, 1H), 5.59 (dd, J=1.9, 9.9 Hz, 1H), 6.10-6.23 (m, 2H), 6.65 (s, 1H), 7.45 (s, 1H).

Example 20

Production of N$^\alpha$-tert-butoxycarbonyl-N$^\pi$-methyl-L-histidine benzyl ester The title compound (1.3 g, 93%) was produced as crystals starting from N$^\alpha$-tert-butoxycarbonyl-N$^\pi$-methyl-L-histidine (1.0 g, 3.7 mmol), benzyl alcohol (0.4 g, 4.4 mmol), WSC.HCl (0.8 g, 4.4 mmol), DMAP (0.04 g, 0.36 mmol) and methylene chloride (14 mL) in the same manner as in the case of N$^\alpha$-tert-butoxycarbonyl-N$^\pi$-methyl-L-histidine neopentyl ester.

¹H-NMR (DMSO-d₆) δ: 1.35 (s, 9H), 2.93 (dd, J=9.7, 15.3 Hz, 1H), 3.02 (dd, J=5.3, 15.3 Hz, 1H), 3.52 (s, 3H), 4.24-4.28 (m, 1H), 5.11 (dd, J=12.7, 18.7 Hz, 2H), 6.66 (s, 1H), 7.31-7.38 (m, 5H), 7.41 (d, J=8.0 Hz, 1H), 7.48 (s, 1H).

Example 21

Production of N$^\pi$-methyl-L-histidine benzyl ester dihydrochloride

The title compound (1.8 g, 99%) was produced as crystals starting from N$^\alpha$-tert-butoxycarbonyl-N$^\pi$-methyl-L-histidine benzyl ester (2.0 g, 5.4 mmol), a 4 mol/L hydrogen chloride-dioxane solution (14 mL, 54.3 mmol HCl) and methylene chloride (30 mL) in the same manner as in the case of N$^\pi$-methyl-L-histidine methyl ester dihydrochloride.

¹H-NMR (DMSO-d₆) δ: 3.38-3.40 (m, 2H), 3.81 (s, 3H), 4.49-4.51 (m, 1H), 5.25 (s, 2H), 6.45-6.55 (br, 2H), 7.36-7.41 (m, 5H), 7.56 (s, 1H), 9.08 (s, 2H), 9.11 (s, 1H).

Example 22

Production of N$^\alpha$-acryloyl-N$^\pi$-methyl-L-histidine benzyl ester [Compound 8]

The title compound (0.8 g, 47%) was produced as an oily substance starting from N$^\pi$-methyl-L-histidine benzyl ester dihydrochloride (1.8 g, 5.4 mmol), potassium hydrogen carbonate (2.2 g, 21.7 mmol), acryloyl chloride (0.8 mL, 9.5 mmol) and water (30 mL) in the same manner as in the case of N$^\alpha$-acryloyl-N$^\pi$-methyl-L-histidine methyl ester.

¹H-NMR (DMSO-d₆) δ: 2.99 (dd, J=8.7, 15.4 Hz, 1H), 3.08 (dd, J=5.7, 15.4 Hz, 1H), 3.51 (s, 3H), 4.65-4.67 (m, 1H), 5.08-5.16 (m, 2H), 5.64 (dd, J=1.9, 10.2 Hz, 1H), 6.11 (dd, J=1.9, 17.1 Hz, 1H), 6.29 (dd, J=10.2, 17.1 Hz, 1H), 6.64 (s, 1H), 7.31-7.38 (m, 5H), 7.49 (s, 1H), 8.66 (d, J=7.7 Hz, 1H).

Example 23

Production of N$^\alpha$-tert-butoxycarbonyl-N$^\pi$-methyl-L-histidine 4-methylbenzyl ester The title compound (5.0 g, 89%) was produced as crystals starting from N$^\alpha$-tert-butoxycarbonyl-N$^\pi$-methyl-L-histidine (4.0 g, 14.9 mmol), 4-methylbenzyl alcohol (2.0 g, 16.5 mmol), WSC.HCl (3.2 g, 16.5 mmol), DMAP (0.16 g, 1.4 mmol) and methylene chloride (50 mL) in the same manner as in the case of N$^\alpha$-tert-butoxycarbonyl-N$^\pi$-methyl-L-histidine neopentyl ester.

$^1$H-NMR (DMSO-d$_6$) δ: 1.33 (s, 9H), 2.28 (s, 3H), 2.89 (dd, J=9.8, 15.2 Hz, 1H), 2.98 (dd, J=5.2, 15.2 Hz, 1H), 3.50 (s, 3H), 4.20-4.24 (m, 1H), 5.02-5.08 (m, 2H), 6.64 (s, 1H), 7.16 (d, J=7.9 Hz, 2H), 7.20 (d, J=7.9 Hz, 2H), 7.36 (d, J=8.0 Hz, 1H), 7.46 (s, 1H).

Example 24

Production of N$^\pi$-methyl-L-histidine 4-methylbenzyl ester dihydrochloride

The title compound (3.8 g, 99%) was produced as an amorphous solid starting from N$^\alpha$-tert-butoxycarbonyl-N$^\pi$-methyl-L-histidine 4-methylbenzyl ester (4.1 g, 11.0 mmol), a 4 mol/L hydrogen chloride-dioxane solution (28 mL, 110 mmol HCl) and methylene chloride (70 mL) in the same manner as in the case of N$^\pi$-methyl-L-histidine methyl ester dihydrochloride.

$^1$H-NMR (DMSO-d$_6$) δ: 2.32 (s, 3H), 3.35-3.37 (m, 2H), 3.80 (s, 3H), 4.46-4.48 (m, 1H), 5.20 (s, 2H), 7.20 (d, J=7.8 Hz, 2H), 7.29 (d, J=7.8 Hz, 2H), 7.53 (s, 1H), 9.02 (s, 2H), 9.10 (s, 1H).

Example 25

Production of N$^\alpha$-acryloyl-N$^\pi$-methyl-L-histidine 4-methylbenzyl ester [Compound 9]

The title compound (0.8 g, 23%) was produced as an oily substance starting from N$^\pi$-methyl-L-histidine 4-methylbenzyl ester dihydrochloride (3.8 g, 11.0 mmol), potassium hydrogen carbonate (4.4 g, 44.0 mmol), acryloyl chloride (1.6 mL, 19.2 mmol) and water (35 mL) in the same manner as in the case of N$^\alpha$-acryloyl-N$^\pi$-methyl-L-histidine methyl ester.

$^1$H-NMR (DMSO-d$_6$) δ: 2.30 (s, 3H), 2.98 (dd, J=8.8, 15.4 Hz, 1H), 3.06 (dd, J=5.5, 15.4 Hz, 1H), 3.51 (s, 3H), 4.62-4.65 (m, 1H), 5.03-5.10 (m, 2H), 5.63 (d, J=10.1 Hz, 1H), 6.12 (d, J=17.1 Hz, 1H), 6.21 (dd, J=10.1, 17.1 Hz, 1H), 6.62 (s, 1H), 7.16-7.21 (m, 2H), 7.48 (s, 1H), 8.67 (d, J=7.7 Hz, 1H).

Example 26

Production of N$^\alpha$-tert-butoxycarbonyl-N$^\pi$-methyl-L-histidine 4-chlorobenzyl ester The title compound (3.7 g, 84%) was produced as crystals starting from N$^\alpha$-tert-butoxycarbonyl-N$^\pi$-methyl-L-histidine (3.0 g, 11.1 mmol), 4-chlorobenzyl alcohol (1.7 g, 11.9 mmol), WSC.HCl (2.3 g, 11.9 mmol), DMAP (0.12 g, 1.0 mmol) and methylene chloride (42 mL) in the same manner as in the case of N$^\alpha$-tert-butoxycarbonyl-N$^\pi$-methyl-L-histidine neopentyl ester.

$^1$H-NMR (DMSO-d$_6$) δ: 1.34 (s, 9H), 2.92 (dd, J=9.7, 15.3 Hz, 1H), 3.00 (dd, J=5.4, 15.3 Hz, 1H), 3.52 (s, 3H), 4.23-4.27 (m, 1H), 5.07-5.14 (m, 2H), 6.65 (s, 1H), 7.35 (d, J=8.3 Hz, 1H), 7.40-7.43 (m, 2H), 7.48 (s, 1H).

Example 27

Production of N$^\pi$-methyl-L-histidine 4-chlorobenzyl ester dihydrochloride

The title compound (5.4 g, 99%) was produced as crystals starting from N$^\alpha$-tert-butoxycarbonyl-N$^\pi$-methyl-L-histidine 4-chlorobenzyl ester (5.8 g, 14.8 mmol), a 4 mol/L hydrogen chloride-dioxane solution (37 mL, 148 mmol HCl) and methylene chloride (90 mL) in the same manner as in the case of N$^\pi$-methyl-L-histidine methyl ester dihydrochloride.

$^1$H-NMR (DMSO-d$_6$) δ: 3.37-3.39 (m, 2H), 3.82 (s, 3H), 4.49-4.51 (m, 1H), 5.24 (s, 2H), 7.44-7.48 (m, 4H), 7.58 (s, 1H), 9.06 (s, 2H), 9.11 (s, 1H).

Example 28

Production of N$^\alpha$-acryloyl-N$^\pi$-methyl-L-histidine 4-chlorobenzyl ester [Compound 10]

The title compound (1.0 g, 21%) was produced as an oily substance starting from N$^\pi$-methyl-L-histidine 4-chlorobenzyl ester dihydrochloride (5.0 g, 13.6 mmol), potassium hydrogen carbonate (5.4 g, 54.4 mmol), acryloyl chloride (1.9 mL, 23.9 mmol) and water (70 mL) in the same manner as in the case of N$^\alpha$-acryloyl-N$^\pi$-methyl-L-histidine methyl ester.

$^1$H-NMR (DMSO-d$_6$) δ: 2.99 (dd, J=8.7, 15.4 Hz, 1H), 3.07 (dd, J=5.8, 15.4 Hz, 1H), 3.52 (s, 3H), 4.63-4.65 (m, 1H), 5.07-5.15 (m, 2H), 5.64 (dd, J=1.7, 10.2 Hz, 1H), 6.11 (dd, J=1.7, 17.1 Hz, 1H), 6.28 (dd, J=10.2, 17.1 Hz, 1H), 6.63 (s, 1H), 7.34 (d, J=8.3 Hz, 2H), 7.43 (d, J=8.3 Hz, 2H), 7.49 (s, 1H), 8.66 (d, J=7.8 Hz, 1H).

Example 29

Production of N$^\alpha$-tert-butoxycarbonyl-N$^\pi$-methyl-L-histidine 4-tert-butylbenzyl ester The title compound (4.3 g, 94%) was produced as an oily substance starting from N$^\alpha$-tert-butoxycarbonyl-N$^\pi$-methyl-L-histidine (3.0 g, 11.1 mmol), 4-tert-butylbenzyl alcohol (2.1 g, 12.3 mmol), WSC.HCl (2.3 g, 12.3 mmol), DMAP (0.12 g, 1.0 mmol) and methylene chloride (70 mL) in the same manner as in the case of N$^\alpha$-tert-butoxycarbonyl-N$^\pi$-methyl-L-histidine neopentyl ester.

$^1$H-NMR (DMSO-d$_6$) δ: 1.23 (s, 9H), 1.34 (s, 9H), 2.88-2.93 (m, 1H), 2.98-3.01 (m, 1H), 3.51 (s, 3H), 4.22-4.23 (m, 1H), 5.03-5.10 (m, 2H), 6.65 (s, 1H), 7.25 (d, J=8.0 Hz, 2H), 7.38 (d, J=8.0 Hz, 2H), 7.48 (s, 1H).

Example 30

Production of N$^\pi$-methyl-L-histidine 4-tert-butylbenzyl ester dihydrochloride The title compound (3.1 g, 77%) was produced as an amorphous solid starting from N$^\alpha$-tert-butoxycarbonyl-N$^\pi$-methyl-L-histidine 4-tert-butylbenzyl ester (4.3 g, 10.4 mmol), a 4 mol/L hydrogen chloride-dioxane solution (26 mL, 104 mmol HCl) and methylene chloride (70 mL) in the same manner as in the case of N$^\pi$-methyl-L-histidine methyl ester dihydrochloride.

$^1$H-NMR (DMSO-d$_6$) δ: 1.28 (s, 9H), 3.37-3.39 (m, 2H), 4.47-4.49 (m, 1H), 5.21 (s, 2H), 7.33 (d, J=8.3 Hz, 2H), 7.41 (d, J=8.3 Hz, 2H), 7.57 (s, 1H), 9.06 (s, 2H), 9.12 (s, 1H).

Example 31

Production of N$^\alpha$-acryloyl-N$^\pi$-methyl-L-histidine 4-tert-butylbenzyl ester [Compound 11]

The title compound (0.4 g, 15%) was produced as an oily substance starting from N$^\pi$-methyl-L-histidine 4-tert-butylbenzyl ester dihydrochloride (3.1 g, 8.0 mmol), potassium hydrogen carbonate (3.2 g, 32.0 mmol), acryloyl chloride (1.1 mL, 13.9 mmol) and water (40 mL) in the same manner as in the case of N$^\alpha$-acryloyl-N$^\pi$-methyl-L-histidine methyl ester.

$^1$H-NMR (DMSO-d$_6$) δ: 1.27 (s, 9H), 2.98-3.00 (m, 1H), 3.05-3.08 (m, 1H), 3.51 (s, 3H), 4.63-4.65 (m, 1H), 5.02-5.11 (m, 2H), 5.64 (dd, J=1.8, 10.2 Hz, 1H), 6.11 (dd, J=1.8, 17.2 Hz, 1H), 6.28 (dd, J=10.2, 17.2 Hz, 1H), 6.63 (s, 1H), 7.24 (d, J=8.1 Hz, 2H), 7.38 (d, J=8.1 Hz, 2H), 7.49 (s, 1H), 8.63 (d, J=7.8 Hz, 1H).

Example 32

Production of N$^\alpha$-tert-butoxycarbonyl-N$^\pi$-methyl-L-histidine phenethyl ester To a suspension of N$^\alpha$-tert-butoxycarbonyl-N$^\pi$-methyl-L-histidine (10.0 g, 37.1 mmol) and phenethyl alcohol (5.0 g, 40.8 mmol) in methylene chloride (150 mL) were added WSC.HCl (7.8 g, 40.8 mmol) and DMAP (0.40 g, 3.3 mmol) at 0° C. After the mixture was stirred at room temperature for 20 hours, water was added thereto, the mixture was extracted with ethyl acetate and the organic layer was washed with water and dried over anhydrous sodium sulfate. The solvent was evaporated therefrom in vacuo and the resulting residue was purified by silica gel column chromatography (chloroform:methanol=25:1) to give the title compound (10.9 g, 78%) as crystals.

$^1$H-NMR (DMSO-d$_6$) δ: 1.35 (s, 9H), 2.83-2.88 (m, 4H), 3.49 (s, 3H), 4.15-4.18 (m, 1H), 4.21-4.27 (m, 2H), 6.61 (s, 1H), 7.21-7.34 (m, 6H), 7.48 (s, 1H).

Example 33

Production of N$^\pi$-methyl-L-histidine phenethyl ester dihydrochloride

Into a solution of N$^\alpha$-tert-butoxycarbonyl-N$^\pi$-methyl-L-histidine phenethyl ester (5.0 g, 13.4 mmol) in methylene chloride (100 mL) was dropped a 4 mol/L hydrogen chloride-dioxane solution (34 mL, corresponding to 134 mmol of hydrogen chloride) at room temperature. After the mixture was stirred for 4 hours, the solvent was evaporated therefrom in vacuo to give the title compound (4.7 g, 99%) as an oily substance.

$^1$H-NMR (DMSO-d$_6$) δ: 2.92 (t, J=6.9 Hz, 2H), 3.27-3.29 (m, 2H), 3.80 (s, 3H), 4.37-4.42 (m, 3H), 7.22-7.33 (m, 5H), 7.47 (s, 1H), 8.95 (br, 3H), 9.09 (s, 1H).

Example 34

Production of N$^\alpha$-acryloyl-N$^\pi$-methyl-L-histidine phenethyl ester [Compound 12]

The title compound (1.0 g, 43%) was produced as crystals starting from N$^\pi$-methyl-L-histidine phenethyl ester dihydrochloride (2.5 g, 7.2 mmol), potassium hydrogen carbonate (2.9 g, 2.89 mmol), acryloyl chloride (1.0 mL, 12.6 mmol) and water (30 mL) in the same manner as in the case of N$^\alpha$-acryloyl-NT-methyl-L-histidine methyl ester.

$^1$H-NMR (DMSO-d$_6$) δ: 2.84-2.95 (m, 4H), 3.49 (s, 3H), 4.23-4.27 (m, 2H), 4.55-4.57 (m, 1H), 5.64 (dd, J=2.0, 10.2 Hz, 1H), 6.01 (dd, J=2.0, 17.1 Hz, 1H), 6.27 (dd, J=10.2, 17.1 Hz, 1H), 6.58 (s, 1H), 7.20-7.30 (m, 5H), 7.48 (s, 1H), 8.58 (d, J=7.8 Hz, 1H).

Example 35

Production of N$^\alpha$-tert-butoxycarbonyl-N$^\pi$-methyl-L-histidine 4-methoxyphenethyl ester The title compound (5.4 g, 90%) was produced as an amorphous solid starting from N$^\alpha$-tert-butoxycarbonyl-N$^\pi$-methyl-L-histidine (4.0 g, 14.9 mmol), 4-methoxyphenethyl alcohol (2.5 g, 16.4 mmol), WSC.HCl (3.1 g, 16.4 mmol), DMAP (0.16 g, 1.3 mmol) and methylene chloride (90 mL) in the same manner as in the case of N$^\alpha$-tert-butoxycarbonyl-N$^\pi$-methyl-L-histidine neopentyl ester.

$^1$H-NMR (DMSO-d$_6$) δ: 1.35 (s, 9H), 2.77-2.80 (m, 2H), 2.81-2.91 (m, 2H), 3.51 (s, 3H), 3.72 (s, 3H), 4.15-4.22 (m, 3H), 6.62 (s, 1H), 6.85 (d, J=8.5 Hz, 2H) 7.16 (d, J=8.5 Hz, 2H), 7.33 (d, J=8.1 Hz, 1H), 7.49 (s, 1H).

Example 36

Production of N$^\pi$-methyl-L-histidine 4-methoxyphenethyl ester dihydrochloride The title compound (4.8 g, 99%) was produced as an amorphous solid starting from N$^\alpha$-tert-butoxycarbonyl-N$^\pi$-methyl-L-histidine 4-methoxyphenethyl ester (5.2 g, 12.9 mmol), a 4 mol/L hydrogen chloride-dioxane solution (32 mL, 129 mmol HCl) and methylene chloride (100 mL) in the same manner as in the case of N$^\pi$-methyl-L-histidine methyl ester dihydrochloride.

$^1$H-NMR (DMSO-d$_6$) δ: 2.84-2.87 (m, 2H), 3.29-3.31 (m, 2H), 3.73 (s, 3H), 3.81 (s, 3H), 4.30-4.40 (m, 3H), 6.87 (d, J=8.6 Hz, 2H), 7.19 (d, J=8.6 Hz, 2H), 7.49 (s, 1H), 8.98 (s, 1H), 9.12 (s, 1H).

Example 37

Production of N$^\alpha$-acryloyl-N$^\pi$-methyl-L-histidine 4-methoxyphenethyl ester [Compound 13]

The title compound (1.0 g, 23%) was produced as an oily substance starting from N$^\pi$-methyl-L-histidine 4-methoxyphenethyl ester dihydrochloride (4.6 g, 12.2 mmol), potassium hydrogen carbonate (4.9 g, 48.8 mmol), acryloyl chloride (1.7 mL, 21.4 mmol) and water (50 mL) in the same manner as in the case of N$^\alpha$-acryloyl-N$^\pi$-methyl-L-histidine methyl ester.

$^1$H-NMR (DMSO-d$_6$) δ: 2.76-2.78 (m, 2H), 2.89-2.95 (m, 2H), 3.49 (s, 3H), 3.70 (s, 3H), 4.17-4.20 (m, 2H), 4.54-4.55 (m, 1H), 5.61-5.64 (m, 1H), 6.07-6.11 (m, 1H), 6.24-6.29 (m, 1H), 6.57 (s, 1H), 6.83 (d, J=8.6 Hz, 2H), 7.13 (d, J=8.6 Hz, 2H), 7.48 (s, 1H), 8.57 (d, J=7.9 Hz, 1H).

Example 38

Production of N$^\alpha$-tert-butoxycarbonyl-N$^\pi$-methyl-L-histidine 4-methylphenethyl ester The title compound (4.3 g, 75%) was produced as an amorphous solid starting from N$^\alpha$-tert-butoxycarbonyl-N$^\pi$-methyl-L-histidine (4.0 g, 14.9 mmol), 4-methylphenethyl alcohol (2.3 mL, 16.4 mmol), WSC.HCl (3.1 g, 16.4 mmol), DMAP (0.16 g, 1.3 mmol) and methylene chloride (90 mL) in the same manner as in the case of N$^\alpha$-tert-butoxycarbonyl-N$^\pi$-methyl-L-histidine neopentyl ester.

$^1$H-NMR (DMSO-d$_6$) δ: 1.35 (s, 9H), 2.26 (s, 3H), 2.78-2.87 (m, 4H), 3.50 (s, 3H), 4.16-4.23 (m, 3H), 6.61 (s, 1H), 7.09-7.13 (m, 4H), 7.32 (d, J=8.1 Hz, 1H), 7.48 (s, 1H).

Example 39

Production of N$^\pi$-methyl-L-histidine 4-methylphenethyl ester dihydrochloride The title compound (3.9 g, 98%) was produced as crystals starting from N$^\alpha$-tert-butoxycarbonyl-N$^\pi$-methyl-L-histidine 4-methylphenethyl ester (4.3 g, 11.1 mmol), a 4 mol/L hydrogen chloride-dioxane solution (28 mL, 111 mmol HCl) and methylene chloride (70 mL) in the same manner as in the case of N$^\pi$-methyl-L-histidine methyl ester dihydrochloride.

$^1$H-NMR (DMSO-d$_6$) δ: 2.27 (s, 3H), 2.87 (t, J=6.8 Hz, 2H), 3.27-3.32 (m, 2H), 3.81 (s, 1H), 4.32-4.40 (m, 3H), 7.12-7.16 (m, 4H), 7.48 (s, 1H), 9.03 (s, 2H), 9.14 (s, 1H).

Example 40

Production of N$^\alpha$-acryloyl-N$^\pi$-methyl-L-histidine 4-methylphenethyl ester [Compound 14]

The title compound (0.3 g, 8%) was produced as an oily substance starting from N$^\pi$-methyl-L-histidine 4-methylphenethyl ester dihydrochloride (3.9 g, 10.8 mmol), potassium hydrogen carbonate (4.3 g, 43.2 mmol), acryloyl chloride (1.5 mL, 18.9 mmol) and water (50 mL) in the same manner as in the case of N$^\alpha$-acryloyl-N$^\pi$-methyl-L-histidine methyl ester.

$^1$H-NMR (DMSO-d$_6$) δ: 2.26 (s, 3H), 2.80 (t, J=6.7 Hz, 2H), 2.89 (dd, J=8.8, 15.5, 1H), 2.97 (dd, J=5.6, 15.5 Hz, 1H), 3.50 (s, 3H), 4.20-4.23 (m, 2H), 4.53-4.56 (m, 1H), 5.64 (dd, J=1.7, 10.2, 1H), 6.10 (dd, J=1.7, 17.1 Hz, 1H), 6.27 (dd, J=10.2, 17.1 Hz, 1H), 6.58 (s, 1H), 7.08-7.12 (m, 4H), 7.49 (s, 1H), 8.58 (d, J=7.8 Hz, 1H).

Example 41

Production of N$^\alpha$-tert-butoxycarbonyl-N$^\pi$-methyl-L-histidine 4-chlorophenethyl ester The title compound (6.0 g, 99%) was produced as an amorphous solid starting from N$^\alpha$-tert-butoxycarbonyl-N$^\pi$-methyl-L-histidine (4.0 g, 14.9 mmol), 4-chlorophenethyl alcohol (2.6 g, 16.4 mmol), WSC.HCl (3.1 g, 16.4 mmol); DMAP (0.16 g, 1.3 mmol) and methylene chloride (90 mL) in the same manner as in the case of N$^\alpha$-tert-butoxycarbonyl-N$^\pi$-methyl-L-histidine neopentyl ester.

$^1$H-NMR (DMSO-d$_6$) δ: 1.34 (s, 9H), 2.79-2.89 (m, 4H), 3.50 (s, 3H), 4.10-4.26 (m, 3H), 6.61 (s, 1H), 7.28 (d, J=8.3 Hz, 2H), 7.32 (d, J=8.7 Hz, 1H), 7.34 (d, J=8.3 Hz, 2H), 7.48 (s, 1H).

Example 42

Production of N$^\pi$-methyl-L-histidine 4-chlorophenethyl ester dihydrochloride The title compound (5.0 g, 93%) was produced as an amorphous solid starting from N$^\alpha$-tert-butoxycarbonyl-methyl-L-histidine 4-chlorophenethyl ester (5.8 g, 14.2 mmol), a 4 mol/L hydrogen chloride-dioxane solution (36 mL, 142 mmol HCl) and methylene chloride (100 mL) in the same manner as in the case of N$^\pi$-methyl-L-histidine methyl ester dihydrochloride.

$^1$H-NMR (DMSO-d$_6$) δ: 2.91-2.94 (m, 2H), 3.28-3.30 (m, 2H), 3.81 (s, 3H), 4.35-4.40 (m, 3H), 7.32 (d, J=8.3 Hz, 2H), 7.37 (d, J=8.3 Hz, 2H), 7.52 (s, 1H), 8.95 (s, 1H), 9.10 (s, 1H).

Example 43

Production of N$^\alpha$-acryloyl-N$^\pi$-methyl-L-histidine 4-chlorophenethyl ester [Compound 15]

The title compound (0.4 g, 9%) was produced as an oily substance starting from N$^\pi$-methyl-L-histidine 4-chlorophenethyl ester dihydrochloride (4.8 g, 12.6 mmol), potassium hydrogen carbonate (5.0 g, 50.4 mmol), acryloyl chloride (1.8 mL, 22.1 mmol) and water (50 mL) in the same manner as in the case of N$^\alpha$-acryloyl-N$^\pi$-methyl-L-histidine methyl ester.

$^1$H-NMR (DMSO-d$_6$) δ: 2.83-2.98 (m, 4H), 3.50 (s, 3H), 4.23-4.26 (m, 2H), 4.53-4.57 (m, 1H), 5.63-5.65 (m, 1H), 6.08-6.12 (m, 1H), 6.24-6.29 (m, 1H), 6.58 (s, 1H), 7.26 (d, J=8.3 Hz, 2H), 7.33 (d, J=8.3 Hz, 2H), 7.49 (s, 1H), 8.58 (d, J=7.8 Hz, 1H).

Example 44

Production of N$^\alpha$-tert-butoxycarbonyl-N$^\pi$-methyl-L-histidine 4-tert-butylphenethyl ester The title compound (9.5 g, 99%) was produced as an oily substance starting from N$^\alpha$-tert-butoxycarbonyl-N$^\pi$-methyl-L-histidine (6.0 g, 22.3 mmol), 4-tert-butylphenethyl alcohol (4.5 g, 24.5 mmol), WSC.HCl (4.7 g, 24.5 mmol), DMAP (0.25 g, 2.0 mmol) and methylene chloride (120 mL) in the same manner as in the case of N$^\alpha$-tert-butoxycarbonyl-N$^\pi$-methyl-L-histidine neopentyl ester.

$^1$H-NMR (DMSO-d$_6$) δ: 1.25 (s, 9H), 1.35 (s, 9H), 2.79-2.87 (m, 4H), 3.50 (s, 3H), 4.17-4.25 (m, 3H), 6.61 (s, 1H), 7.17 (d, J=8.1 Hz, 2H), 7.30-7.34 (m, 3H), 7.48 (s, 1H).

Example 45

Production of N$^\pi$-methyl-L-histidine 4-tert-butylphenethyl ester dihydrochloride The title compound (7.3 g, 82%) was produced as an amorphous solid starting from N$^\alpha$-tert-butoxycarbonyl-N$^\pi$-methyl-L-histidine 4-tert-butylphenethyl ester (9.5 g, 22.1 mmol), a 4 mol/L hydrogen chloride-dioxane solution (55 mL, 221 mmol HCl) and methylene chloride (140 mL) in the same manner as in the case of N$^\pi$-methyl-L-histidine methyl ester dihydrochloride.

$^1$H-NMR (DMSO-d$_6$) δ: 1.26 (s, 9H), 2.88 (d, J=7.1 Hz, 2H), 3.29-3.33 (m, 2H), 3.81 (s, 3H), 4.33-4.40 (m, 3H), 7.20 (d, J=8.1 Hz, 2H), 7.33 (d, J=8.1 Hz, 2H), 7.49 (s, 1H), 9.13 (s, 1H).

Example 46

Production of N$^\alpha$-acryloyl-N$^\pi$-methyl-L-histidine 4-tert-butylphenethyl ester [Compound 16]

The title compound (0.6 g, 9%) was produced as an oily substance starting from N$^\pi$-methyl-L-histidine 4-tert-butylphenethyl ester dihydrochloride (7.3 g, 18.1 mmol), potassium hydrogen carbonate (7.3 g, 72.6 mmol), acryloyl chloride (2.6 mL, 31.8 mmol) and water (80 mL) in the same manner as in the case of N$^\alpha$-acryloyl-N$^\pi$-methyl-L-histidine methyl ester.

$^1$H-NMR (DMSO-d$_6$) δ: 1.25 (s, 9H), 2.81 (t, J=6.8 Hz, 2H), 2.90-2.96 (m, 2H), 4.20-4.24 (m, 2H), 4.55-4.57 (m, 1H), 5.64 (dd, J=2.0, 10.2 Hz, 1H), 6.10 (dd, J=2.0, 17.0 Hz,

1H), 6.28 (dd, J=10.2, 17.0 Hz, 1H), 6.58 (s, 1H), 7.15 (d, J=8.2 Hz, 2H), 7.30 (d, J=8.2 Hz, 2H), 7.49 (s, 1H), 8.59 (d, J=7.8 Hz, 1H).

Example 47

Production of $N^\alpha$-tert-butoxycarbonyl-$N^\pi$-methyl-L-histidine 1-(cyclohexyloxycarbonyloxy)ethyl ester Into a suspension of potassium carbonate (2.1 g, 14.9 mmol) in DMF (20 mL) was dropped a solution of $N^\alpha$-tert-butoxycarbonyl-$N^\pi$-methyl-L-histidine (2.0 g, 7.4 mmol) in DMF (20 mL) at 0° C. followed by stirring at room temperature for 0.5 hour. 1-Chloroethylcyclohexyl carbonate (1.8 g, 8.9 mmol) was dropped into the above mixture at 0° C. followed by stirring at room temperature for 20 hours. The reaction solution was poured over ice water, the mixture was extracted with ethyl acetate and the organic layer was dried over anhydrous sodium sulfate. The residue prepared by evaporation of the solvent therefrom in vacuo was purified by silica gel column chromatography (chloroform methanol=30:1) to give the title compound (1.7 g, 53%) as an oily substance.

MS (EI) m/z: 440 (M⁺). ¹H-NMR (DMSO-d₆) δ: 1.32-1.44 (m, 15H), 1.62-1.64 (m, 2H), 1.81-1.83 (m, 2H), 2.89-2.94 (m, 2H), 3.31 (s, 3H), 3.52-3.53 (m, 3H), 4.21-4.23 (m, 1H), 4.54-4.56 (m, 1H), 6.62-6.66 (m, 2H), 7.39-7.41 (m, 1H), 7.48-7.49 (m, 1H).

Example 48

Production of $N^\pi$-methyl-L-histidine 1-(cyclohexyloxycarbonyloxy)ethyl ester dihydrochloride The title compound (1.1 g, 67%) was produced as an oily substance starting from $N^\alpha$-tert-butoxycarbonyl-$N^\pi$-methyl-L-histidine 1-(cyclohexyloxycarbonyloxy)ethyl ester (1.7 g, 4.0 mmol), a 4 mol/L hydrogen chloride-dioxane solution (10 mL, 40.0 mmol HCl) and methylene chloride (25 mL) in the same manner as in the case of $N^\pi$-methyl-L-histidine methyl ester dihydrochloride.

¹H-NMR (DMSO-d₆) δ: 1.22-1.50 (m, 6H), 1.63-1.65 (m, 2H), 1.83-1.85 (m, 2H), 3.32-3.39 (m, 5H), 3.84-3.86 (m, 3H), 4.48-4.52 (m, 1H), 4.55-4.60 (m, 1H), 6.71-6.74 (m, 1H), 7.56-7.59 (m, 1H), 9.01-9.12 (m, 3H).

Example 49

Production of $N^\alpha$-acryloyl-$N^\pi$-methyl-L-histidine 1-(cyclohexyloxycarbonyloxy)ethyl ester [Compound 17]

The title compound (0.3 g, 29%) was produced as an oily substance starting from $N^\pi$-methyl-L-histidine 1-(cyclohexyloxycarbonyloxy)ethyl ester dihydrochloride (1.1 g, 2.6 mmol), potassium hydrogen carbonate (1.1 g, 10.6 mmol), acryloyl chloride (0.37 mL, 4.6 mmol) and water (20 mL) in the same manner as in the case of $N^\alpha$-acryloyl-$N^\pi$-methyl-L-histidine methyl ester.

¹H-NMR (DMSO-d₆) δ: 1.31-1.45 (m, 6H), 1.63-1.65 (m, 2H), 1.81-1.83 (m, 2H), 2.94-3.03 (m, 2H), 3.32 (s, 3H), 3.52-3.54 (m, 3H), 4.55-4.61 (m, 2H), 5.62-5.65 (m, 1H), 6.08-6.12 (m, 1H), 6.24-6.27 (m, 1H), 6.61-6.66 (m, 2H), 7.49-7.50 (m, 1H), 8.63-8.66 (m, 1H).

Example 50

Production of $N^\alpha$-tert-butoxycarbonyl-$N^\pi$-methyl-L-histidine ethoxycarbonylmethyl ester The title compound (4.8 g, 91%) was produced as an oily substance starting from $N^\alpha$-tert-butoxycarbonyl-$N^\pi$-methyl-L-histidine (4.0 g, 14.9 mmol), ethyl chloroacetate (1.9 mL, 17.8 mmol), potassium carbonate (4.3 g, 31.3 mmol) and DMF (50 mL) in the same manner as in the case of $N^\alpha$-tert-butoxycarbonyl-$N^\pi$-methyl-L-histidine 1-(cyclohexyl-oxycarbonyloxy)ethyl ester.

¹H-NMR (DMSO-d₆) δ: 1.21 (t, J=6.9 Hz, 3H), 1.35 (s, 9H), 2.88-2.93 (m, 1H), 3.03-3.06 (m, 1H), 3.55 (s, 3H), 4.14 (q, J=6.9 Hz, 2H), 4.30-4.32 (m, 1H), 4.68-4.76 (m, 2H), 6.69 (s, 1H), 7.41 (d, J=8.3 Hz, 1H), 7.50 (s, 1H).

Example 51

Production of $N^\pi$-methyl-L-histidine ethoxycarbonylmethyl ester dihydrochloride The title compound (3.0 g, 67%) was produced as crystals starting from $N^\alpha$-tert-butoxycarbonyl-$N^\pi$-methyl-L-histidine ethoxycarbonylmethyl ester (4.8 g, 13.6 mmol), a 4 mol/L hydrogen chloride-dioxane solution (34 mL, 136 mmol HCl) and methylene chloride (80 mL) in the same manner as in the case of $N^\pi$-methyl-L-histidine methyl ester dihydrochloride.

¹H-NMR (DMSO-d₆) δ: 1.23 (t, J=7.0 Hz, 3H), 3.39-3.40 (m, 2H), 3.87 (s, 3H), 4.18 (q, J=7.0 Hz, 2H), 4.58-4.60 (m, 1H), 4.84-4.92 (m, 2H), 7.62 (s, 1H), 9.07 (s, 2H), 9.14 (s, 1H).

Example 52

Production of $N^\alpha$-acryloyl-$N^\pi$-methyl-L-histidine ethoxycarbonylmethyl ester [Compound 18]

The title compound (1.0 g, 36%) was produced as an oily substance starting from $N^\pi$-methyl-L-histidine ethoxycarbonylmethyl ester dihydrochloride (2.9 g, 8.8 mmol), potassium hydrogen carbonate (3.5 g, 35.4 mmol), acryloyl chloride (1.2 mL, 15.5 mmol) and water (40 mL) in the same manner as in the case of $N^\alpha$-acryloyl-$N^\pi$-methyl-L-histidine methyl ester.

¹H-NMR (DMSO-d₆) δ: 1.19 (t, J=7.2 Hz, 3H), 2.97 (dd, J=9.5, 15.6 Hz, 1H), 3.13 (dd, J=4.9 Hz, 15.6 Hz, 1H), 3.54 (s, 3H), 4.14 (q, J=7.2 Hz, 2H), 4.72-4.75 (m, 3H), 5.64 (dd, J=2.1, 10.0 Hz, 1H), 6.10 (dd, J=2.1, 17.1 Hz, 1H), 6.27 (dd, J=10.0, 17.1 Hz, 1H), 6.68 (s, 1H), 7.50 (s, 1H), 8.67 (d, J=8.1 Hz, 1H).

Example 53

Production of $N^\alpha$-acryloyl-$N^\pi$-methyl-L-histidine carboxylmethyl ester [Compound 19]

Into a solution of $N^\alpha$-acryloyl-$N^\pi$-methyl-L-histidine ethoxycarbonylmethyl ester (0.7 g, 2.3 mmol) in ethanol (25 mL) was dropped a 1 mol/L aqueous sodium hydroxide (3.4 mL, 3.4 mmol) at room temperature and the mixture was stirred for 1 hour as it was. Water was added to the residue prepared by evaporation of the solvent therefrom in vacuo, the mixture was made neutral using p-toluenesulfonic acid beads of a polystyrene bonding type and the beads were filtered off. The filtrate was freeze-dried to give the title compound (0.3 g, 64%) as crystals.

¹H-NMR (DMSO-d₆) δ: 2.89 (dd, J=8.1, 15.6 Hz, 1H), 3.06 (dd, J=4.7, 15.6 Hz, 1H), 3.52 (s, 3H), 3.78 (s, 2H), 4.41-4.42 (m, 1H), 5.56 (d, J=10.2 Hz, 1H), 6.05 (d, J=17.0 Hz, 1H), 6.34 (dd, J=10.2, 17.0 Hz, 1H), 6.63 (s, 1H), 7.49 (s, 1H), 8.17 (d, J=7.9 Hz, 1H).

Example 54

Production of $N^\alpha$-tert-butoxycarbonyl-$N^\pi$-ethyl-L-histidine phenethyl ester To a suspension of $N^\alpha$-tert-butoxycarbonyl-$N^\pi$-ethyl-L-histidine (9.8 g, 34.6 mmol) and phenethyl alcohol (4.6 g, 38.1 mmol) in methylene chloride (200 mL) were added WSC.HCl (7.3 g, 38.1 mmol) and DMAP (0.38 g, 3.1 mmol) at 0° C. After the mixture was stirred at room temperature for 20 hours, the reaction mixture was washed with water and dried over anhydrous sodium sulfate. The residue prepared by evaporation of the solvent therefrom in vacuo was purified by silica gel column chromatography (chloroform:methanol=80:1) to give the title compound (12.8 g, 99%) as an oily substance.

¹H-NMR (DMSO-d₆) δ: 1.26 (t, J=7.2 Hz, 3H), 1.35 (s, 9H), 2.82-2.87 (m, 4H), 3.85 (q, J=7.2 Hz, 2H), 4.23-4.27 (m, 3H), 6.60 (s, 1H), 7.22-7.35 (m, 6H), 7.55 (s, 1H).

Example 55

Production of $N^\pi$-ethyl-L-histidine phenethyl ester dihydrochloride

Into a solution of $N^\alpha$-tert-butoxycarbonyl-$N^\pi$-ethyl-L-histidine phenethyl ester (12.8 g, 34.3 mmol) in methylene chloride (200 mL) was dropped a 4 mol/L hydrogen chloride-dioxane solution (86 mL, corresponding to 343 mmol of hydrogen chloride) at room temperature. After the mixture was stirred for 4 hours, the solvent was evaporated therefrom in vacuo to give the title compound (11.1 g, 90%) as an oily substance.

¹H-NMR (DMSO-d₆) δ: 1.39 (t, J=7.3 Hz, 3H), 2.91 (t, J=6.8 Hz, 2H), 3.28-3.32 (m, 2H), 4.17 (q, J=7.3 Hz, 2H), 4.37-4.39 (m, 3H), 7.23-7.31 (m, 5H), 7.51 (s, 1H), 8.90-9.00 (br, 2H), 9.17 (s, 1H).

Example 56

Production of $N^\alpha$-3-phenylacryloyl-$N^\pi$-ethyl-L-histidine phenethyl ester [Compound 20]

Into a solution of $N^\pi$-ethyl-L-histidine phenethyl ester dihydrochloride (7.8 g, 21.6 mmol) in methylene chloride (100 mL) was dropped triethylamine (12.0 mL, 86.4 mmol) at 0° C. followed by stirring for 15 minutes. A solution of cinnamoyl chloride (4.3 g, 26.0 mmol) in methylene chloride (30 mL) was further dropped thereinto at 0° C. followed by stirring at room temperature for 24 hours. After the reaction solution was washed with water, the organic layer was dried over anhydrous sodium sulfate. The residue prepared by evaporation of the solvent therefrom in vacuo was purified by silica gel column chromatography (chloroform methanol=60:1) to give the title compound (5.1 g, 56%) as an oily substance.

¹H-NMR (DMSO-d₆) δ: 1.28 (t, J=7.3 Hz, 3H), 2.87 (t, J=6.7 Hz, 2H), 2.93-2.97 (m, 2H), 3.87 (q, J=7.3 Hz, 2H), 4.27-4.29 (m, 2H), 4.61-4.63 (m, 1H), 6.63 (s, 1H), 6.69 (d, J=15.8 Hz, 1H), 7.19-7.27 (m, 5H), 7.38-7.47 (m, 4H), 7.57-5.58 (m, 3H), 8.61 (d, J=7.8 Hz, 1H).

Example 57

Production of $N^\alpha$-tert-butoxycarbonyl-$N^\pi$-benzyl-L-histidine phenethyl ester To a suspension of $N^\alpha$-tert-butoxycarbonyl-$N^\pi$-benzyl-L-histidine (8.0 g, 23.0 mmol) and phenethyl alcohol (3.1 g, 25.0 mmol) in methylene chloride (150 mL) were added WSC.HCl (4.8 g, 25.0 mmol) and DMAP (0.30 g, 2.1 mmol) at 0° C. After the mixture was stirred at room temperature for 20 hours, water was added thereto, the mixture was extracted with ethyl acetate and the organic layer was washed with water and dried over anhydrous sodium sulfate. The residue prepared by evaporation of the solvent therefrom in vacuo was purified by silica gel column chromatography (chloroform:methanol=25:1) to give the title compound (8.5 g, 99%) as an oily substance.

¹H-NMR (DMSO-d₆) δ: 1.36 (s, 9H), 2.73-2.84 (m, 4H), 4.08-4.11 (m, 2H), 4.18-4.25 (m, 1H), 5.15 (s, 2H), 6.70 (s, 1H), 6.72-7.35 (m, 10H), 7.66 (s, 1H).

Example 58

Production of $N^\pi$-benzyl-L-histidine phenethyl ester dihydrochloride

Into a solution of $N^\alpha$-tert-butoxycarbonyl-$N^\pi$-benzyl-L-histidine phenethyl ester (8.0 g, 17.8 mmol) in methylene chloride (200 mL) was dropped a 4 mol/L hydrogen chloride-dioxane solution (45 mL, corresponding to 178 mmol of hydrogen chloride) at room temperature. After the mixture was stirred for 4 hours, the solvent was evaporated therefrom in vacuo to give the title compound (7.6 g, 99%) as an oily substance.

¹H-NMR (DMSO-d₆) δ: 2.88 (t, J=6.7 Hz, 2H), 3.10-3.26 (m, 2H), 4.22 (t, J=6.7 Hz, 1H), 4.31-4.37 (m, 2H), 5.56 (s, 2H), 7.20-7.42 (m, 10H), 7.57 (s, 1H), 9.01 (br, NH), 9.31 (s, 1H).

Example 59

Production of $N^\alpha$-acryloyl-$N^\pi$-benzyl-L-histidine phenethyl ester [Compound 21]

Into a solution of $N^\pi$-benzyl-L-histidine phenethyl ester dihydrochloride (7.0 g, 16.6 mmol) in methylene chloride (200 mL) was dropped triethylamine (9.3 mL, 66.4 mmol) at 0° C. followed by stirring for 15 minutes. Acryloyl chloride (2.4 mL, 29.1 mmol) was further dropped thereinto at 0° C. followed by stirring at room temperature for 24 hours. The residue prepared by evaporation of the solvent therefrom in vacuo was purified by silica gel column chromatography (chloroform:methanol=19:1) to give the title compound (1.3 g, 19%) as an oily substance.

¹H-NMR (DMSO-d₆) δ: 2.76-2.86 (m, 4H), 4.20-4.25 (m, 2H), 4.44-4.46 (m, 1H), 5.14 and 5.17 (ABq, J=16.1 Hz, 2H), 5.63 (dd, J=2.0, 10.2 Hz, 1H), 6.10 (dd, J=2.0, 17.1 Hz, 1H), 6.26 (dd, J=10.2, 17.1 Hz, 1H), 6.67 (s, 1H), 7.06-7.36 (m, 10H), 7.67 (s, 1H), 8.56 (d, J=7.8 Hz, 1H).

Example 60

Production of $N^\alpha$-tigloyl-$N^\pi$-methyl-L-histidine phenethyl ester [Compound 22]

To an aqueous solution of $N^\pi$-methyl-L-histidine phenethyl ester dihydrochloride (4.6 g, 13.4 mmol) was added potassium hydrogen carbonate (5.4 g, 53.6 mmol) under cooling with ice, then tigloyl chloride (2.6 mL, 23.5 mmol) was dropped thereinto and the mixture was stirred as it was for 45 minutes. After the reaction, the mixture was extracted with ethyl acetate and the organic layer was washed with water and dried over anhydrous sodium sulfate. The residue prepared by evaporation of the solvent therefrom in vacuo was purified by silica gel column chromatography (chloroform:methanol=18:1) to give the title compound (2.2 g, 46%), as an oily substance.

$^1$H-NMR (DMSO-d$_6$) δ: 1.69-1.73 (m, 6H), 2.85 (t, J=6.7 Hz, 2H), 2.95 (d, J=7.4 Hz, 2H), 3.50 (s, 3H), 4.21-4.27 (m, 2H), 4.46 (dt, J=7.7, 7.4 Hz, 1H), 6.29-6.31 (m, 1H), 6.60 (s, 1H), 7.20-7.30 (m, 5H), 7.47 (s, 1H), 8.09 (d, J=7.7 Hz, 1H).

Example 61

Production of N$^α$-crotonoyl-N$^π$-methyl-L-histidine phenethyl ester [Compound 23]

To a solution of N$^π$-methyl-L-histidine phenethyl ester dihydrochloride (9.3 g, 26.8 mmol) in methylene chloride (120 mL) was added triethylamine (18.7 mL, 134 mmol) under cooling with ice and then crotonic acid (2.8 g, 32.2 mmol) was further added thereto. After that, a solution of DCC (6.6 g, 32.2 mmol) in methylene chloride (24 mL) was dropped thereinto. After the mixture was stirred at room temperature for 24 hours, one half of the solvent was evaporated therefrom in vacuo, acetone was added thereto and the mixture was allowed to stand for one night in a refrigerator. Triethylamine hydrochloride and DC urea were filtered off and the solvent of the filtrate was evaporated therefrom in vacuo. The resulting oily residue was purified by silica gel column chromatography (chloroform:methanol=19:1) to give the title compound (1.3, 14%) as an oily substance.

$^1$H-NMR (DMSO-d$_6$) δ: 1.78-1.80 (m, 3H), 2.84-2.96 (m, 4H), 3.49 (s, 3H), 4.22-4.27 (m, 2H), 4.51-4.56 (m, 1H), 5.94-5.97 (m, 1H), 6.58 (s, 1H), 6.60-6.67 (m, 1H), 7.20-7.30 (m, 5H), 7.47 (s, 1H), 8.34 (d, J=7.9 Hz, 1H).

Example 62

Production of N$^α$-tert-butoxycarbonyl-N$^π$-methyl-L-histidine diphenylmethyl ester To a suspension of N$^α$-tert-butoxycarbonyl-N$^π$-methyl-L-histidine (18.3 g, 68.1 mmol) and benzhydrol (15.1 g, 81.7 mmol) in methylene chloride (300 mL) were added WSC.HCl (15.7 g, 81.7 mmol) and DMAP (0.75 g, 6.1 mmol) at 0° C. After the mixture was stirred at room temperature for 24 hours, the reaction mixture was washed with water and dried over anhydrous sodium sulfate. The residue prepared by evaporation of the solvent therefrom in vacuo was purified by silica gel column chromatography (chloroform:methanol=60:1) to give the title compound (26.3 g, 89%) as an oily substance.

$^1$H-NMR (DMSO-d$_6$) δ: 1.36 (s, 9H), 2.91-2.96 (m, 1H), 3.03-3.07 (m, 1H), 3.50 (s, 3H), 4.33-4.35 (m, 1H), 6.64 (s, 1H), 6.80 (s, 1H), 7.26-7.51 (m, 12H).

Example 63

Production of N$^π$-methyl-L-histidine diphenylmethyl ester dihydrochloride

Into a solution of N$^α$-tert-butoxycarbonyl-N$^π$-methyl-L-histidine diphenylmethyl ester (26.7 g, 60.4 mmol) in methylene chloride (400 mL) was dropped a 4 mol/L hydrogen chloride-dioxane solution (151 mL, 603 mmol HCl) at room temperature. After the mixture was stirred for 2 hours, the crystals separated out therefrom were filtered to give the title compound (19.0 g, 77%).

$^1$H-NMR (DMSO-d$_6$) δ: 3.31-3.43 (s, 2H), 3.77 (s, 3H), 4.62-4.64 (m, 1H), 6.91 (s, 1H), 7.30-7.56 (m, 11H), 9.02-9.04 (br, 4H).

Example 64

Production of N$^α$-acryloyl-N$^π$-methyl-L-histidine diphenylmethyl ester [Compound 24]

Into a solution of N$^π$-methyl-L-histidine diphenylmethyl ester dihydrochloride (2.0 g, 4.9 mmol) in methylene chloride (40 mL) was dropped triethylamine (2.7 mL, 19.6 mmol) at 0° C. followed by stirring for 15 minutes as it was. Acryloyl chloride (0.48 mL, 5.9 mmol) was further dropped thereinto at 0° C. followed by stirring at room temperature for 1 hour. The reaction mixture was washed with water and dried over anhydrous sodium sulfate. The residue prepared by evaporation of the solvent therefrom in vacuo was purified by silica gel column chromatography (chloroform methanol=30:1) to give the title compound (0.32 g, 17%) as an amorphous solid.

$^1$H-NMR (DMSO-d$_6$) δ: 2.97-3.01 (m, 1H), 3.10-3.14 (m, 1H), 3.50 (s, 3H), 4.74-4.78 (m, 1H), 5.65 (dd, J=1.7, 10.3 Hz, 1H), 6.12 (dd, J=1.7, 17.1 Hz, 1H), 6.29 (dd, J=10.3, 17.1 Hz, 1H), 6.59 (s, 1H), 6.79 (s, 1H), 7.27-7.46 (m, 1H), 8.68 (d, J=8.0 Hz, 1H).

Example 65

Production of N$^α$-tert-butoxycarbonyl-N$^π$-methyl-L-histidine 1,1-dimethyl-2-phenethyl ester The title compound (3.9 g, 37%) was produced as an oily substance starting from N$^α$-tert-butoxycarbonyl-N$^π$-methyl-L-histidine (7.0 g, 26.0 mmol), 2-methyl-1-phenyl-2-propanol (4.4 mL, 28.6 mmol), WSC.HCl (5.5 g, 28.6 mmol), DMAP (0.3 g, 2.3 mmol) and methylene chloride (150 mL) in the same manner as in the case of N$^α$-tert-butoxycarbonyl-N$^π$-methyl-L-histidine diphenylmethyl ester.

$^1$H-NMR (DMSO-d$_6$) δ: 1.33-1.36 (m, 15H), 2.82-2.84 (m, 1H), 2.87-2.88 (m, 1H), 2.95 (d, J=13.3 Hz, 1H), 3.62 (d, J=13.3 Hz, 1H), 3.51 (s, 3H), 4.05-4.10 (m, 1H), 6.60 (s, 1H), 7.20-7.30 (m, 6H), 7.47 (s, 1H).

Example 66

Production of N$^π$-methyl-L-histidine 1,1-dimethyl-2-phenethyl ester dihydrochloride The title compound (2.7 g, 75%) was produced as crystals starting from N$^α$-tert-butoxycarbonyl-N$^π$-methyl-L-histidine 1,1-dimethyl-2-phenethyl ester (3.9 g, 9.7 mmol), a 4 mol/L hydrogen chloride-dioxane solution (24 mL, 97.4 mmol HCl) and methylene chloride (80 mL) in the same manner as in the case of N$^π$-methyl-L-histidine diphenylmethyl ester dihydrochloride.

$^1$H-NMR (DMSO-d$_6$) δ: 1.42 (s, 6H), 3.04 (s, 2H), 3.20-3.25 (m, 1H), 3.30-3.34 (m, 1H), 3.82 (s, 3H), 4.26-4.28 (m, 1H), 7.22-7.34 (m, 5H), 7.47 (s, 1H), 8.80-9.00 (br, 2H), 9.11 (s, 1H).

Example 67

Production of N$^\alpha$-acryloyl-N$^\pi$-methyl-L-histidine 1,1-dimethyl-2-phenethyl ester [Compound 25]

To a solution of N$^\pi$-methyl-L-histidine 1,1-dimethyl-2-phenethyl ester dihydrochloride (2.7 g, 7.2 mmol) in water (40 mL) was added potassium hydrogen carbonate (2.9 g, 28.8 mmol) at 0° C. followed by stirring for 15 minutes as it was. After that, acryloyl chloride (1.0 mL, 12.6 mmol) was added thereto at 0° C. followed by stirring for 1 hour as it was. Methylene chloride was added to the residue prepared by evaporation of the solvent therefrom in vacuo and then the insoluble matters were removed therefrom. The filtrate was dried over anhydrous sodium sulfate in the presence of a small amount of silica gel and the solvent was evaporated therefrom in vacuo to give the title compound (0.5 g, 20%) as an oily substance.

$^1$H-NMR (DMSO-d$_6$) δ: 1.33 (s, 3H), 1.38 (s, 3H), 2.86-2.99 (m, 4H), 3.52 (s, 3H), 4.48-4.53 (m, 1H), 5.63 (dd, J=1.8, 10.2 Hz, 1H), 6.11 (dd, J=1.8, 17.0 Hz, 1H), 6.32 (dd, J=10.2, 17.0 Hz, 1H), 6.58 (s, 1H), 7.18-7.28 (m, 5H), 7.48 (s, 1H), 8.55 (d, J=7.9 Hz, 1H).

Example 68

Production of 2-methoxymethoxybenzaldehyde

Into a solution of tert-butoxy potassium (30.0 g, 0.27 mol) in DMF (200 mL) was dropped a solution of 2-hydroxybenzaldehyde (30.0 g, 0.25 mol) in DMF (100 mL) at 0° C. followed by stirring at room temperature for 1 hour. After addition of DMF (200 mL) thereto, a solution of chloromethylmethyl ether (21 mL, 0.27 mol) in DMF (200 mL) was dropped thereinto at 0° C. following by stirring at room temperature for 20 hours. The reaction mixture was poured over ice water followed by extracting with diethyl ether. The organic layer was washed with a 10% aqueous sodium hydroxide and a saturated saline solution successively and then dried over anhydrous sodium sulfate. The solvent was evaporated therefrom in vacuo to give the title compound (32.6 g, 80%) as an oily substance.

$^1$H-NMR (DMSO-d$_6$) δ: 3.47 (s, 3H), 5.39 (s, 2H), 7.14-7.17 (m, 1H), 7.32 (d, J=7.5 Hz, 1H), 7.64-7.67 (m, 1H), 7.74-7.76 (m, 1H), 10.44 (s, 1H).

Example 69

Production of 2-methoxymethoxycinnamic acid

To a solution of 2-methoxymethoxybenzaldehyde (15.0 g, 90.3 mmol) in pyridine (80 mL) were added malonic acid (18.8 g, 181 mmol) and piperidine (1.0 mL, 9.0 mmol) followed by heating to reflux for 6 hours. Water was added to the residue prepared by evaporation of the solvent therefrom in vacuo and the mixture was acidified with a diluted hydrochloric acid. The crystals separated out therefrom were filtered and washed with water to give the title compound (16.5 g, 88%).

Mp. 133-134° C. $^1$H-NMR (DMSO-d$_6$) δ: 3.41 (s, 3H), 5.32 (s, 2H), 6.54 (d, J=16.2 Hz, 1H), 7.03-7.06 (m, 1H), 7.18 (d, J=8.4 Hz, 1H), 7.37-7.40 (m, 1H), 7.72 (d, J=7.7 Hz, 1H), 7.89 (d, J=16.2 Hz, 1H), 12.38 (s, 1H).

Example 70

Production of N$^\alpha$-[3-(2-methoxymethoxyphenypacryloyl]-N$^\pi$-methyl-L-histidine phenethyl ester To a suspension of N$^\pi$-methyl-L-histidine phenethyl ester dihydrochloride (5.0 g 14.4 mmol) in methylene chloride (150 mL) were added 2-methoxymethoxycinnamic acid (3.6 g, 17.3 mmol), triethylamine (4.4 mL, 31.7 mmol) and WSC.HCl (3.3 g, 17.3 mmol) at 0° C. and the mixture was stirred at room temperature for 6 hours. After the reaction mixture was washed with water, the organic layer was dried over anhydrous sodium sulfate. The residual oily substance prepared by evaporation of the solvent therefrom in vacuo was purified by silica gel column chromatography (chloroform:methanol=30:1) to give the title compound (6.2 g, 92%) as an oily substance.

$^1$H-NMR (DMSO-d$_6$) δ: 2.86-2.89 (m, 2H), 2.96-3.00 (m, 2H), 3.41 (s, 3H), 3.53 (s, 3H), 4.26-4.30 (m, 2H), 4.64-4.66 (m, 1H), 5.30 (s, 1H), 6.64 (s, 1H), 6.75 (d, J=16.0 Hz, 1H), 7.05-7.07 (m, 1H), 7.17-7.35 (m, 7H), 7.51 (s, 1H), 7.56-7.58 (m, 1H), 7.77 (d, J=16.0 Hz, 1H), 8.65 (d, J=7.9 Hz, 1H).

Example 71

Production of N$^\alpha$-[3-(2-hydroxyphenyl)acryloyl]-N$^\pi$-methyl-L-histidine phenethyl ester hydrochloride [Compound 26]

Into a solution of N$^\alpha$-[3-(2-methoxymethoxyphenyl)-acryloyl]-N$^\pi$-methyl-L-histidine phenethyl ester (6.2 g, 13.3 mmol) in methylene chloride (100 mL) was dropped a 4 mol/L hydrogen chloride-dioxane solution (10 mL, corresponding to 40 mmol of HCl) and the mixture was stirred for 22 hours as it was. To the residue prepared by evaporation of the solvent therefrom in vacuo was added diethyl ether and the crystals separated out therefrom were filtered to give the title compound (5.3 g, 94%).

Mp. 64-65° C. $^1$H-NMR (DMSO-d$_6$) δ: 2.90 (t, J=6.7 Hz, 1H), 3.08 (dd, J=6.5, 15.8 Hz, 1H), 3.17 (d, J=5.1, 15.8 Hz, 1H), 3.78 (s, 1H), 4.31 (t, J=6.7 Hz, 2H), 4.72-4.76 (m, 1H), 6.73 (d, J=15.9 Hz, 1H), 6.81-6.84 (m, 1H), 6.97 (d, J=8.1 Hz, 1H), 7.18-7.21 (m, 2H), 7.26-7.27 (m, 4H), 7.39-7.43 (m, 2H), 7.65 (d, J=15.9 Hz, 1H), 8.78 (d, J=7.9 Hz, 1H), 9.05 (s, 1H), 10.26 (s, 1H).

Example 72

Test for Analgesic Effect (1)

In a test for analgesic effect, a pathological animal model called SART stressed mouse which shows a chronic hyperalgesia state was used. Loading of SART (Specific Alternation of Rhythm in Temperature) stress or repetitive cold stress was conducted in accordance with a method of Kita, et al. (*Nippon Yakurigaku Zasshi*, Vol. 71, pages 195 to 210, 1975). In a constant-temperature vessel for breeding, a breeding environment temperature for male mice of ddY strain was alternately changed at 4° C. and 24° C. every one hour from 10 a.m. until 5 p.m. and kept at 4° C. from 5 p.m. to 10 a.m. of the next morning. Breeding was conducted for 5 days where water and feed were freely taken by the mice so as to load a repetitive cold stress and, after that, the mice were subjected to the test. Before and after 30 minutes from administration of the test substance, analgesic threshold value was measured by a modified Randall-Selitto method (Tail pressure method; *Nippon Yakurigaku Zasshi*, Vol. 72, pages 573 to 584, 1976).

Thus, Using a Randall-Selitto analgesic effect measuring device where a pressing piece was modified for mouse tail, a pressure stimulation was applied at the rate of 16 g/second to the site which was 1.5 cm to the front end from tail root of the mouse and pressurized weight (g) showing an escaping or squeaking reaction was measured and adopted as a pain threshold value. In a normal control group, the pain threshold value was about 125 to 135 g while, in the SART control group to which SART stress was loaded, pain reaction was noted at the pressurized weight (pain threshold value) of about 80 to 85 g whereby the SART stressed mice were in hyperalgesia. A value (analgesic coefficient) where the pain threshold of the test substance administration group was divided by the pain threshold of the SART control group was calculated and the analgesic effect of the test substance was confirmed. Thus, when the test substance had no effect at all, said value was 1.0 and, as the effect became stronger, the value of the analgesic coefficient increased as 1.1, 1.2 and 1.3. Significant difference between the two groups was determined by a statistic processing of the pain threshold values and the analgesic coefficient was calculated as a mean value of the pain threshold values.

As to the test animals, male mice of ddY strain of four weeks age (one group comprised ten mice) were used. A carboxylic acid type of the compound of the present invention as a test substance was administered at a dose of 25 ng per mouse into the lateral ventricle whereupon its analgesic effect was measured. An example (mean value of the analgesic coefficients) of the result of the above test is shown in Table 1. When an analgesic effect test using the SART stressed mouse which is pathologic model animal showing chronic hyperalgesia was conducted, the carboxylic acid type of the compounds of the present invention (A, B and C of the carboxylic acid type are generated by the metabolism of Compound 1-Compound 19, Compound 23 and Compound 20 of the present invention in vivo, respectively) showed an excellent analgesic effect. In a significance test for pain threshold values, Dunnett's multiple comparison test was used and the result in the test substances in the table showed a significant difference in $p<0.05$ as compared with the SART stressed mouse control group in any case.

TABLE 1

| Test substance | Analgesic coefficient |
| --- | --- |
| Carboxylic acid type A | 1.33 |
| Carboxylic acid type B | 1.23 |
| Carboxylic acid type C | 1.14 |

Carboxylic acid type A: $N^{\alpha}$-acryloyl-$N^{\pi}$-methyl-L-histidine
Carboxylic acid type B: $N^{\alpha}$-crotonoyl-$N^{\pi}$-methyl-L-histidine
Carboxylic acid type C: $N^{\alpha}$-3-phenylpropenoyl-$N^{\pi}$-ethyl-L-histidine Further, when Carboxylic acid type A was intraperitoneally administered (100 µg/kg) to mice, the pain threshold value in the SART control group was 79.0 kg while, in the test substance administration group, it was 97.8 g (analgesic coefficient: 1.24) whereby a significant improving effect for hyperalgesia was noted. In the case of oral administration in mice, a significant analgesic action was showed at a dose of 3 and 10 mg/kg having a peak after 30 minutes from the oral administration and $ED_{50}$ value determined from the improving rate upon the action was in peak was 2.7 mg/kg. On the contrary, when an analgesic test was conducted for anserine and carnosine as test substances by the above-mentioned administration into the lateral ventricle, no significant analgesic action was found.

Example 73

Test for Analgesic Effect (2)

A test for analgesic effect was conducted using a Chung model rat which is a neuropathic pain model. As to the test animal, male rats of Wistar strain of nine weeks age were used and model rats were prepared in accordance with the method of Kim and Chung (*Pain*, vol. 50, pages 355 to 363, 1992). Thus, under anesthetization with pentobarbital (40 mg/kg, intraperitoneal administration), rat L5 spinal nerve was exposed and L5 dorsal root ganglion periphery side was strongly ligated using 5-0 silk yarn. The animals were placed in a transparent acrylate cage whose bottom was made of wire net, a 50% reaction threshold value was calculated by an up-down method using a von Frey filament (manufactured by North Coast Medical Inc.) according to the methods of Chaplan, et al. (*J. Neurosci. Method*, vol. 53, pages 55 to 63, 1994) and by Lee, et al. (*J. Neurophysiol.*, vol. 81, pages 2226 to 2233, 1999) and measurement of allodynia was conducted. Before injury of spinal nerve, the 50% reaction threshold value was measured twice and the animals where the threshold value was outside the standard were excluded from the operation for spinal nerve injury. After 14, 17 and 28 days from the spinal nerve injury, the 50% reaction threshold values were measured and the animals which showed a stable decrease in the threshold and also showed a threshold of 1 g to less than 4 g after 28 days were used for the test. Those test animals were made into groups of seven animals so that the mean value of 50% reaction threshold after 28 days from the nerve injury as an index became nearly the same in each group.

The carboxylic acid type of the compounds of the present invention as a test substance was intraperitoneally administered in a single dose while, a 0.5% CMC-Na/physiological saline solution was administered similarly to a nerve injury control group. After 30 minutes from the administration of the test substance, allodynia was measured to calculate a 50% reaction threshold value. With regard to a significance test, Paired t-test was conducted for comparison between before and after the nerve injury and Dunnett's multiple comparison test was used for comparison among multiple groups of the nerve injury control group and the test substance administration group. In any of the cases, the results showed significant difference in $p<0.05$.

As a result of the above analgesic effect test, the mean value of 50% reaction threshold at the normal stage before the L5 spinal nerve injury was 15.00 g (n=42) while, after 28 days from the nerve injury, it lowered to 2.46 g (n=42; before constituting the group). As the result of 50% reaction threshold value before and after the spinal nerve injury, it was confirmed that a mechanical allodynia was obviously occurred. On the basis of above confirmation, Carboxylic acid type A as a test substance was intraperitoneally administered (100 µg/kg) in a single dose and an analgesic effect test using Chung model rats was carried out. As a result, the mean value of 50% reaction threshold in the nerve injury control group was 2.48 (n=7, after constituting the group) before administration of the solvent while, after 30 minutes from the administration of the solvent, it was 2.70 g whereby no big change was observed between the stages before and after the administration. On the contrary, the 50% reaction threshold value of the test substance administration group was 9.60 g. Similarly, Carboxylic acid type D ($N^{\alpha}$-acryloyl-$N^{\pi}$-benzyl-L-histidine) as a test substance, which is generated by the metabolism of Compound 21 in vivo, was intraperitoneally administered (400 µg/kg) in a single dose. As a result, the mean value of 50% reaction threshold in the nerve injury control group was 2.61 g before administration of the solvent and it was 2.81 g after 30 minutes from the administration of the solvent. On the contrary, the 50% reaction threshold value of the test substance administration group was 7.32 g Accordingly, in both test substance administration groups of Carboxylic acid type A and D, a significant increase in the threshold as compared with the nerve injury control group was showed whereby a strong anti-allodynia action of the carboxylic acid type of the compounds of the present invention or an excellent analgesic action to neuropathic pain was observed. In the case of oral administration, Carboxylic acid type A showed a significant anti-allodynia action to a mechanical allodynia of Chung's model rats at the dose of 10 mg/kg having a peak after 30 minutes from the oral administration, and the $ED_{50}$ value determined from the improving rate at the peak of the action was 2.4 mg/kg.

Example 74

Test for Analgesic Effect (3)

According to the same manner as in the above Test for Analgesic Effect (2), each of Compound 12 of the present invention (3 mg/kg, 10 mg/kg) and Carboxylic acid substance A of the compound of the present invention (10 mg/kg) was orally administered in a single dose as the test substance to Chung model rats. Allodynia after 0, 15, 30, 60 and 120 minutes from the administration was measured for each of the test substance administration group and the nerve injury control group whereupon a 50% reaction threshold value was calculated.

An example of the above test result is shown in FIG. 1. As compared with the nerve injury control group, Compound 12 of the present invention and Carboxylic acid type A of the compound of the present invention showed significant anti-allodynia action at the stages of 15, 30 and 60 minutes after the administration. Further, Compound 12 of the present invention by oral administration in a dose of 3 mg/kg showed the similar anti-allodynia action as Carboxylic acid substance A thereof in a dose of 10 mg/kg. Namely, Compound 12 of the present invention clearly showed a stronger anti-allodynia action than another in the same dose of 10 mg/kg. As shown in the result of the kinetics in the blood of rats which will be mentioned below, the above result correlates to the fact that Compound 12 of the present invention is better than Carboxylic acid type A thereof in terms of transmigration into the blood upon oral administration.

Example 75

Test for Analgesic Effect (4)

The compounds of the present invention or the carboxylic acid type thereof were orally administered to mice and a test for an analgesic effect was carried out by means of an acetic acid writhing test. As to the test animals, male mice of ddY strain of four weeks age were subjected to a preliminary breeding and they were used where one group comprised ten mice. Each of the compound of the present invention or the carboxylic acid type thereof as a test substance was orally administered in a single dose while, to a control group, distilled water (water for injection) was administered similarly. After 25 minutes from the administration of the test substance, a 0.7% acetic acid/physiological saline was intraperitoneally administered at the dose of 10 mL/kg. From 5 minutes thereafter, writhing numbers during 10 minutes were counted and a suppressive rate for each mouse was calculated according to the following formula.

Suppressive Rate (%)=[(Mean writhing numbers of the control group)−(Writhing numbers of each mouse)]÷[Mean writhing numbers of the control group]×100

An example of the result of the above test is shown in Table 2. When a test for analgesic effect by an acetic acid writhing test was conducted, Compound 26 of the present invention and the carboxylic acid type of the compounds of the present invention (D and E of the carboxylic acid type are generated by the metabolism of Compound 21 and Compound 22 of the present invention in vivo, respectively) showed an excellent analgesic effect.

TABLE 2

| Test substance | Suppressive Rate (%) |
| --- | --- |
| Compound 26 | 23.8 |
| Carboxylic acid type A | 33.1 |
| Carboxylic acid type C | 27.7 |
| Carboxylic acid type D | 37.9 |
| Carboxylic acid type E | 17.8 |

Carboxylic acid type A: $N^{\alpha}$-acryloyl-$N^{\pi}$-methyl-L-histidine
Carboxylic acid type C: $N^{\alpha}$-3-phenylpropenoyl-$N^{\pi}$-ethyl-L-histidine
Carboxylic acid type D: $N^{\alpha}$-acryloyl-$N^{\pi}$-benzyl-L-histidine
Carboxylic acid type E: $N^{\alpha}$-3-metylcrotonoyl-$N^{\pi}$-methyl-L-histidine Besides the above-mentioned acetic acid writhing test, Carboxylic acid type A showed a significant analgesic action by oral administration of 100 mg/kg against a pain reaction in the second phase of a formalin pain test for rats. For hyperalgesia in osteoarthritis model induced by administration of monoiodoacetic acid into joints of rats, oral administration of 1 mg/kg of Carboxylic acid type A also showed a significant analgesic effect.

Example 76

Test of Kinetics in Blood of Rats

Each of the compound of the present invention and the carboxylic acid type A thereof was dissolved in DMSO, diluted with water. A sample solution (1% DMSO solution) made into 2 mg/mL was orally administered in a single dose to the fasted Wistar strain SPF male rats of seven weeks age using a stomach tube (10 mg/5 mL/kg). At the stages of 0.25, 0.5, 1, 2, 4 and 8 hour(s) after the administration, about 150 µL of the blood was collected from tail vein using a capillary to which heparin was added and said capillary was centrifuged to collect the plasma. Protein was removed from the plasma sample and the supernatant liquid was diluted to prepare each sample solution for the measurement. Concentration of Carboxylic acid type A in each measuring sample solution was quantified (where the unchanged substance of the compound of the present invention was confirmed to be undetected in the blood) and Cmax (maximum drug concentration in plasma) and AUC (area under the blood concentration time curve; 0 to 8 hour(s)) of the compound of the present invention and Carboxylic acid type A thereof were calculated.

An example of the above test result is shown in Table 3 and FIG. 2. For a purpose that the absorption property between those compounds are able to be compared, the values of Cmax and AUC in Table 3 were shown in such a manner that the measured values were converted to the case where the dose was equimolar to Carboxylic acid type A. As compared with Carboxylic acid type A, the compound of the present invention showed high values in both Cmax and AUC and was confirmed that its transmigration into the blood of rats upon the oral administration was very high.

TABLE 3

| Test substance | Cmax (ng/mL) | AUC (ng · hr/mL) |
| --- | --- | --- |
| Compound 1 | 1623.9 | 2027.6 |
| Compound 2 | 2719.4 | 3468.0 |
| Compound 3 | 2074.0 | 2373.9 |
| Compound 4 | 2144.0 | 2641.8 |
| Compound 5 | 2761.6 | 3264.2 |
| Compound 6 | 2407.2 | 2774.6 |
| Compound 9 | 2671.7 | 3750.7 |
| Compound 10 | 2579.9 | 3747.0 |
| Compound 11 | 2207.4 | 4234.6 |
| Compound 12 | 3111.6 | 3971.6 |
| Compound 13 | 3163.4 | 4058.3 |
| Compound 15 | 2391.8 | 3620.6 |
| Compound 16 | 2562.7 | 3601.8 |
| Compound 17 | 2044.3 | 2704.9 |
| Compound 24 | 1495.3 | 2614.2 |
| Carboxylic acid type A | 372.5 | 1339.4 |

Example 77

Test of Kinetics in Blood of Monkeys

Each of the compound of the present invention and Carboxylic acid type A thereof dissolved or suspended in a hydrochloric acid solution was diluted with water. A sample solution made into 6 mg/mL was administered in a single dose to male cynomolgus monkeys of 3 to 4 years age using a disposable catheter and a syringe (30 mg/5 mL/kg). At the stages of before the administration and of 0.25, 0.5, 1, 2, 4, 8 and 24 hour(s) after the administration, the blood was collected from femoral vein using a syringe to which heparin was added followed by subjecting to centrifugation to collect the plasma. Collection of the blood was conducted for three times in total where one collection was done with each blank term of six days for each test substance. Concentration of Carboxylic acid type A in each of the collected plasma samples was quantified by an LC-MS and Cmax (maximum drug concentration in plasma) and AUC (area under blood concentration time curve; 0 to ∞ hour(s)) of the compound of the present invention and Carboxylic acid type A thereof were calculated.

An example of the above test result is shown in Table 4. For a purpose that the absorption property between those compounds are able to be compared, the values of Cmax and AUC in Table 4 were shown in such a manner that the measured values were converted to the case where the dose was equimolar to Carboxylic acid type A. As compared with Carboxylic acid type A, the compound of the present invention showed high values in both Cmax and AUC and was confirmed that its transmigration into the blood of the monkeys upon the oral administration was very high the same as in the above-mentioned case for rats.

TABLE 4

| Test substance | Cmax (ng/mL) | AUC (ng · hr/mL) |
| --- | --- | --- |
| Compound 12 | 4088.2 | 8099.0 |
| Compound 14 | 779.2 | 5133.2 |
| Carboxylic acid type A | 410.8 | 2356.9 |

Example 78

Single Dose Toxicity Test by Administration to Mice

A single dose toxicity test by intraperitoneal administration of the carboxylic acid type of the compounds of the present invention to mice was carried out. Male mice of ddY strain of four weeks age were made into groups of five mice so as to make mean body weight in each group nearly the same. Carboxylic acid type A as a test substance was intraperitoneally administered at the doses of 250 mg/kg, 500 mg/kg and 1,000 mg/kg.

In this toxicity test, no abnormal observation was noted during the observation period from initial administration until 14 days after the administration in any of the doses and no death case was noted as well. Further, after finishing the observation period for 14 days, autopsied organs and tissues of the body were observed by naked eye whereupon no abnormal case was found at all as in the case of the control group (group to which a physiological saline was administered). With regard to changes in the body weight, no significant difference was also noted at all as compared with the control group. From those results, it was found that the carboxylic acid type of the compounds of the present invention showed no toxic affection at all by intraperitoneal administration to mice and was low toxicity. Therefore, it was shown that the compound of the present invention also was low toxicity, which was quickly metabolized to its carboxylic acid type by the action of an esterase in vivo and was present as the low-toxic carboxylic acid type in the blood.

INDUSTRIAL APPLICABILITY

As shown in the above-mentioned various tests for the analgesic effect, the carboxylic acid type of the histidine derivative of the present invention shows an excellent analgesic action in pathological animal models suffering from acute or chronic pain or from neuropathic pain. It has been shown that the compound of the present invention is quickly metabolized to a carboxylic acid type by the action of an esterase in vivo and exists as a carboxylic acid type in the blood whereby said compound exhibits the same pharmacological action as the carboxylic acid type. In fact, it has been also confirmed that the compound of the present invention shows better pharmacological activity (anti-allodynia action) than the corresponding carboxylic acid type (FIG. 1). As such, the compound of the present invention has a very high intermigration into the blood upon oral administration. Therefore, it is very useful as a pharmaceutical agent for the treatment of various acute or chronic pain diseases and of neuropathic pain diseases such as reflex sympathetic dystrophy, postherpetic neuralgia or diabetic neuropathy for which common analgesics such as non-steroidal anti-inflammatory drugs (NSAIDs) are hardly effective.

The invention claimed is:

1. A histidine derivative represented by the following formula (I) or a pharmaceutically acceptable salt or hydrate thereof;

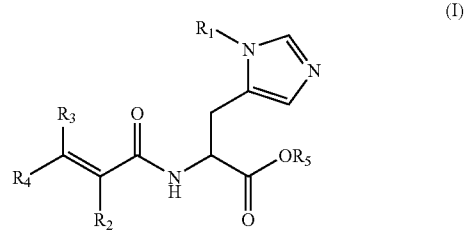

wherein in the formula, $R_1$ is alkyl having 1 to 6 carbon(s) or benzyl which may be substituted with alkyl having 1 to 4 carbon(s) or halogen; $R_2$ is hydrogen or alkyl having 1 to 4 carbon(s); $R_3$ and $R_4$ are same or different and each is hydrogen, alkyl having 1 to 4 carbon(s) or phenyl which may be substituted with any one or two of alkyl having 1 to 6 carbon(s), alkoxy having 1 to 6 carbon(s), hydroxy, halogen, trifluoromethyl, nitro and cyano; and $R_5$ is an alkyl group having 5 to 8 carbons, carboxyl-alkyl having 1 to 4 carbon(s), alkoxy having 1 to 4 carbon(s)-carbonyl-alkyl having 1 to 4 carbon(s), 1-(cyclohexyloxycarbonyloxy)ethyl or one or two phenyl(s)-alkyl having 1 to 4 carbon(s) which may be substituted with alkyl having 1 to 6 carbon(s), alkoxy having 1 to 4 carbon(s) or halogen.

2. The histidine derivative or a pharmaceutically acceptable salt or hydrate thereof according to claim 1, wherein $R_5$ is alkyl having 5 to 8 carbons.

3. The histidine derivative or a pharmaceutically acceptable salt or hydrate thereof according to claim 1, wherein $R_5$ is one or two phenyl(s)-alkyl having 1 to 4 carbon(s) which may be substituted with alkyl having 1 to 6 carbon(s), alkoxy having 1 to 4 carbon(s) or halogen.

4. The histidine derivative or a pharmaceutically acceptable salt or hydrate thereof according to claim 3, wherein $R_5$ is phenylethyl.

5. The histidine derivative or a pharmaceutically acceptable salt or hydrate thereof according to claim 3, wherein $R_5$ is phenylmethyl which is substituted with alkyl having 1 to 6 carbon(s), alkoxy having 1 to 4 carbon(s) or halogen.

6. The histidine derivative or a pharmaceutically acceptable salt or hydrate thereof according to claim 3, wherein $R_5$ is phenylethyl which is substituted with alkyl having 1 to 6 carbon(s), alkoxy having 1 to 4 carbon(s) or halogen.

7. The histidine derivative or a pharmaceutically acceptable salt or hydrate thereof according to claim 3, wherein $R_5$ is diphenylmethyl.

8. The histidine derivative or a pharmaceutically acceptable salt or hydrate thereof according to claim 1, wherein $R_1$ is alkyl having 1 to 6 carbon(s).

9. The histidine derivative or a pharmaceutically acceptable salt or hydrate thereof according to claim 8, wherein $R_3$ is hydrogen.

10. The histidine derivative or a pharmaceutically acceptable salt or hydrate thereof according to claim 9, wherein $R_4$ is hydrogen.

11. The histidine derivative or a pharmaceutically acceptable salt or hydrate thereof according to claim 9, wherein $R_4$ is alkyl having 1 to 4 carbon(s).

12. The histidine derivative or a pharmaceutically acceptable salt or hydrate thereof according to claim 9, wherein $R_4$ is phenyl.

13. The histidine derivative or a pharmaceutically acceptable salt or hydrate thereof according to claim 10, wherein $R_2$ is hydrogen.

14. The histidine derivative or a pharmaceutically acceptable salt or hydrate thereof according to claim 10, wherein $R_2$ is alkyl having 1 to 4 carbon(s).

15. $N^\alpha$-acryloyl-$N^\pi$-methyl-L-histidine phenethyl ester or a pharmaceutically acceptable salt or hydrate thereof.

16. A pharmaceutical preparation containing a histidine derivative represented by the following formula (I) or a pharmaceutically acceptable salt or hydrate thereof as an effective ingredient;

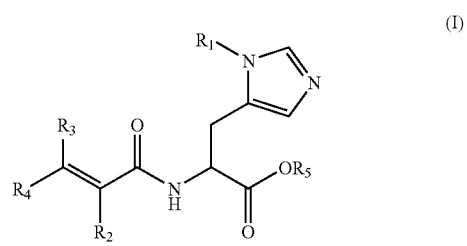

wherein in the formula, $R_1$ is alkyl having 1 to 6 carbon(s) or benzyl which may be substituted with alkyl having 1 to 4 carbon(s) or halogen; $R_2$ is hydrogen or alkyl having 1 to 4 carbon(s); $R_3$ and $R_4$ are same or different and each is hydrogen, alkyl having 1 to 4 carbon(s) or phenyl which may be substituted with any one or two of alkyl having 1 to 6 carbon(s), alkoxy having 1 to 6 carbon(s), hydroxy, halogen, trifluoromethyl, nitro and cyano; and $R_5$ is an alkyl group having 5 to 8 carbons, carboxyl-alkyl having 1 to 4 carbon(s), alkoxy having 1 to 4 carbon(s)-carbonyl-alkyl having 1 to 4 carbon(s), 1-(cyclohexyloxycarbonyloxy)ethyl or one or two phenyl(s)-alkyl having 1 to 4 carbon(s) which may be substituted with alkyl having 1 to 6 carbon(s), alkoxy having 1 to 4 carbon(s) or halogen and a pharmaceutical carrier or diluent.

17. The pharmaceutical preparation according to claim 16, wherein $R_5$ is phenylethyl which may be substituted with alkyl having 1 to 6 carbon(s), alkoxy having 1 to 4 carbon(s) or halogen.

18. The pharmaceutical preparation according to claim 17, wherein said histidine derivative is $N^\alpha$-acryloyl-$N^\pi$-methyl-L-histidine phenethyl ester or a pharmaceutically acceptable salt or hydrate thereof.

19. The pharmaceutical preparation according to claim 16, wherein said histidine derivative is an analgesic and the preparation is in a form of a tablet, capsule, powder or liquid.

* * * * *